(12) United States Patent
Wang et al.

(10) Patent No.: US 12,043,622 B2
(45) Date of Patent: Jul. 23, 2024

(54) CRYSTAL FORM OF COMPOUND FOR INHIBITING THE ACTIVITY OF CDK4/6 AND USE THEREOF

(71) Applicant: Betta Pharmaceuticals Co., Ltd., Zhejiang (CN)

(72) Inventors: Yiqian Wang, Beijing (CN); Chunhui Zhang, Beijing (CN); Jiabing Wang, Beijing (CN); Lieming Ding, Zhejiang (CN)

(73) Assignee: BETTA PHARMACEUTICALS CO., LTD, Zhejiang (CN)

( * ) Notice: Subject to any disclaimer, the term of this patent is extended or adjusted under 35 U.S.C. 154(b) by 738 days.

(21) Appl. No.: 17/254,097

(22) PCT Filed: Jun. 21, 2019

(86) PCT No.: PCT/CN2019/092239
§ 371 (c)(1),
(2) Date: Dec. 18, 2020

(87) PCT Pub. No.: WO2019/242719
PCT Pub. Date: Dec. 26, 2019

(65) Prior Publication Data
US 2021/0261546 A1    Aug. 26, 2021

(51) Int. Cl.
*C07D 471/04* (2006.01)
*A61P 35/00* (2006.01)
(52) U.S. Cl.
CPC ............ *C07D 471/04* (2013.01); *A61P 35/00* (2018.01); *C07B 2200/13* (2013.01)

(58) Field of Classification Search
CPC ... A61P 35/00; C07B 2200/13; C07C 59/255; C07D 471/04
See application file for complete search history.

(56) References Cited

U.S. PATENT DOCUMENTS 11,053,238 B2 * 7/2021 Wang ................. C07D 487/04
2018/0291027 A1   10/2018 Zhao et al.
2018/0305363 A1   10/2018 Liu et al.

FOREIGN PATENT DOCUMENTS

CN    106608879 A    5/2017
CN    107690431 A    2/2018
(Continued)

OTHER PUBLICATIONS

China Patent Office, CN 202111208432.8, First Office Action, Dec. 1, 2022, 10 pages.
(Continued)

*Primary Examiner* — Savitha M Rao
(74) *Attorney, Agent, or Firm* — Umberg Zipser LLP

(57) ABSTRACT

The present invention relates to a salt form of (R)—N-(5-((4-ethylpiperazin-1-yl)methyl)pyridin-2-yl)-5-fluoro-4-(6-fluoro-1-methyl-1,2,3,4-tetrahydrobenzo[4,5]imidazo[1,2-a]pyridin-8-yl)pyrimidin-2-amine (compound I) as shown in structural formula (I) or a crystal form thereof, and also relates to a method for preparing the salt form of compound I and/or the crystal form thereof, a pharmaceutical composition containing the salt form and/or the crystal form, and the use of same in the preparation of drugs for treating
(Continued)

diseases, illnesses or conditions, or a method for treating diseases, illnesses or conditions.

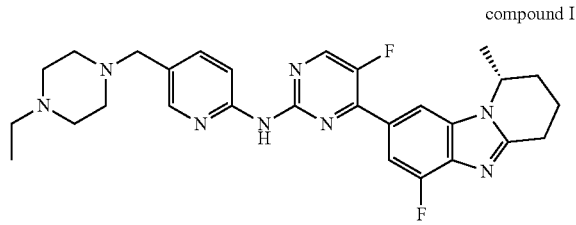

compound I

9 Claims, 6 Drawing Sheets

(56) References Cited

FOREIGN PATENT DOCUMENTS

| CN | 107849012 A | 3/2018 | |
|---|---|---|---|
| CN | 104592251 B | 10/2019 | |
| JP | 2020504747 A | 2/2020 | |
| WO | 2016015604 A1 | 2/2016 | |
| WO | 2016173505 A1 | 11/2016 | |
| WO | 2017102796 A1 | 6/2017 | |
| WO | 2017206924 A1 | 12/2017 | |
| WO | 2018113771 A1 | 6/2018 | |
| WO | WO-2018113771 A1 * | 6/2018 | ........... A61K 31/506 |
| WO | 2019035008 A1 | 2/2019 | |

OTHER PUBLICATIONS

Darkins et al., "Synthesis of Peptidyl Ene Diones: Selective Inactivators of the Cysteine Proteinases," Chem Biol Drug Des 2007; 69: 170-179.
Davies et al., "Convenient in Situ Synthesis of Nonracemic N-protected β-Amino Aldehydes from β-Amino Acids. Applications in Wittig Reactions and Heterocycle Synthesis," Tetrahedron Letters 40 (1999) 1229-1232.
Etxebarria et al., "A general and enantiodivergent method for the asymmetric synthesis of piperidine alkaloids: concise synthesis of (R)-pipecoline, (S)-coniine and other 2-alkylpiperidines," Tetrahedron 63 (2007) 11421-11428.
Järvinen et al., "α-Methyl Polyamines: Efficient Synthesis and Tolerance Studies in Vivo and in Vitro. First Evidence for Dormant Stereospecificity of Polyamine Oxidase," J. Med. Chem. 2006, 49, 399-406.
Jessen et al., "Synthesis of N-protected 14C-Labelled (2E)-5-amino-5-methylhex-2-enoic Acid Analogues," J. Labelled Cpd. Radiopharm. 44, 265-275 (2001).
Wang et al., "Design and synthesis of 4-(2,3-dihydro-1H-benzo[d]pyrrolo[1,2-a]imidazole-7yl)-N-(5-(piperazin-1-ylmethyl)pyridine-2-yl)pyrimidin-2-amin as a highly potent and selective cyclin-dependent kinases 4 and 6 inhibitors and the discovery of structure-activity relationships," Bioorganics & Medicinal Chemistry Letters, 2018; 28:974-978.
Berge et al., "Pharmaceutical Salts," Journal of Pharmaceutical Sciences, Jan. 1977; 66(1):1-19.
Chinese Patent Office; First Office Action; CN 201980037275.3; May 20, 2021; 8 pages.
Crystalline Drugs, ISBN 978-7-117-11571-1, 2009, 7 pages.
Long et al, "Synthetic Process Optimization of CDK4/6 Inhibitor Abemaciclib," Journal of Wuhan Institute of Technology, 2018, 40:149-155.
Patent Protection of Drug Crystal Form, ISBN 978-7-5130-4145-4, 2016, 5 pages.
Eurasian Patent Office; First Office Action; Application No. 202190036; Issued Feb. 8, 2022; 9 pages.

* cited by examiner

CRYSTAL FORM OF COMPOUND FOR INHIBITING THE ACTIVITY OF CDK4/6 AND USE THEREOF

FIELD OF THE INVENTION

The present invention relates to salts and crystal forms of (R)—N-(5-((4-ethylpiperazin-1-yl)methyl)pyridin-2-yl)-5-fluoro-4-(6-fluoro-1-methyl-1,2,3,4-tetrahydrobenzo[4,5]imidazo[1,2-a]pyridin-8-yl)pyrimidin-2-amine; the present invention also relates to the method of preparing the compound and the crystal form thereof and a related intermediate compound, a pharmaceutical composition thereof and use thereof in inhibiting CDK 4/6 activity. The present invention also relates to methods of treating diseases, disorders or conditions associated with CDK 4/6 modulation using at least one of the above compounds or crystal forms and pharmaceutical compositions.

BACKGROUND OF THE INVENTION

Cyclin-dependent kinases (CDKs), a class of serine/threonine protein kinases, are involved in the regulation of cell cycle, transcription initiation and the control of certain metabolic cascades. CDK-cyclin complexes are formed by different CDKs and cyclins, and if CDK activity is not regulated, cell proliferation is out of control, genome instability (increased DNA mutation, chromosome deletion and the like) and chromosome instability (chromosome number change) can be directly or indirectly caused.

CDKs have more than 20 subtypes, CDK1, CDK2, CDK4, CDK6 and the like involved in cell cycle regulation; CDK7, CDK8, CDK9, CDK1 t and the like involved in transcription regulation; and other kinases including CDK3, CDK5, and the like. CDK4/6 (cyclin dependent kinases 4 and 6) is a key factor to regulate the cell cycle, cell cycle mutations associated with cancer mainly exist in G1 and G1/S transformation processes, CDK4/6 and CyclinD combine to form a kinase-active complex, through the phosphorylation of the tumor suppressor gene Rb product pRb, the bound transcription factor E2F is released; transcription of genes associated with S phase is initiated, causing the cells to pass the checkpoint, and transfer from G phase 1 to S phase. CDK4/6-specific activation is closely related to the proliferation of some tumors. Approximately 80% of human tumors have abnormalities in the cyclin D-CDK4/6-INK4-Rb pathway. CDK4/6 inhibitors block the cell cycle in G1 phase and thus act to inhibit tumor proliferation.

The development of a CDK4/6 kinase targeting drug is a significant field, and the antitumor target has the advantages that: (1) Most proliferating cells are dependent on CDK2 or CDK4/6 proliferation, but inhibitors of CDK4/6 do not exhibit the cytotoxicity of "pan-CDK inhibitors", such as myelosuppression and intestinal responses; (2) The preclinical experiments show that if the level of cyclin D is increased or P 16 INK 4a is inactivated, the sensitivity of cells to drugs can be increased, and the targeting of drugs can be increased to some extent due to the phenomenon of tumor cells relative to normal cells.

PCT international application PCT/CN2017/117950 describes a class of benzimidazole derivatives useful as inhibitors of CDK 4/6 protein kinases, most of which are effective in inhibiting CDK 4 and CDK 6. Because there remains an unmet need for therapeutic options for kinase-mediated diseases, we further screen the salt forms of benzimidazole derivatives and their crystal forms to meet the patient's medical needs.

SUMMARY OF THE INVENTION

The present invention relates to a salt and a crystal form of (R)—N-(5-((4-ethylpiperazin-1-yl)methyl)pyridin-2-yl)-5-fluoro-4-(6-fluoro-1-methyl-1,2,3,4-tetrahydrobenzo[4,5]imidazo[1,2-a]pyridin-8-yl)pyrimidin-2-amine as shown in Formula I:

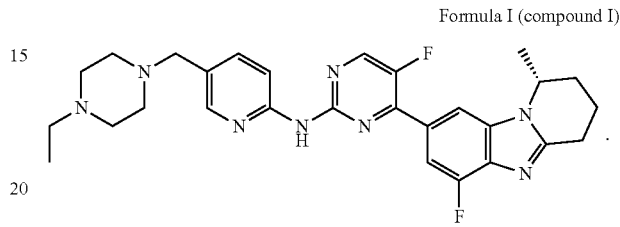

Formula I (compound I)

Salts of Formula I

In some embodiments, the salt is formed by an acid and compound I. The salt can exist in various physical forms. Such as, the salt may be present as a solution, suspension or as a solid. In some embodiments, the salt of the compound is a solid. When the compound is a solid, the compound may be amorphous, crystal or a mixture thereof. The salts of Compound I with the two acids are exemplified below. The salts are tartaric acid salt and methanesulfonic acid salt, respectively. In some embodiments, the tartaric acid salt is L-tartaric acid salt. The structure of L-tartaric acid salt and methanesulfonic acid salt of the compound I is shown as in Formula II and Formula III:

L-Tartaric Acid Salt of Compound I (the Compound of Formula II, Compound II)

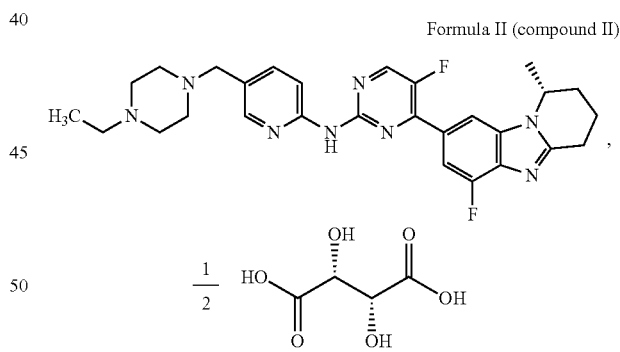

Formula II (compound II)

Methanesulfonic Acid Salt of Compound I (the Compound of Formula III, Compound III)

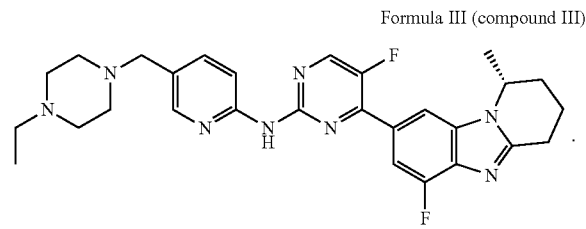 [SMILES: CCN1CCN(Cc2ccc(Nc3ncc(F)c(-c4cc(F)c5nc6n(c5c4)[C@H](C)CCC6)n3)nc2)CC1]

Formula III (compound III)

-continued

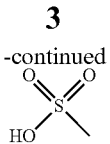

The present invention also provides various crystal forms of the compound II and compound III described above. Such as, Crystal Form A of Compound II The present invention provides a crystal form A of compound II.

In some embodiments, the crystal form A of compound II can be identified by X-ray powder diffraction. In some embodiments, the X-ray powder diffraction pattern of the crystal form A of the compound II has characteristic peaks at the diffraction angle 2θ of 4.4±0.2°, 23.6±0.2° and 26.9±0.2°. For convenience, the present invention is called crystal form A.

In some embodiments, the X-ray powder diffraction pattern of crystal form A has characteristic peaks at the diffraction angle 2θ of 4.4±0.2°, 8.7±0.2°, 10.8±0.2°, 18.4±0.2°, 23.6±0.2° and 26.9±0.2°.

In some embodiments, the X-ray powder diffraction pattern of crystal form A has characteristic peaks at the diffraction angle 2θ of 4.4±0.2°, 8.7±0.2°, 10.8±0.2°, 15.9±0.2°, 18.4±0.2°, 23.6±0.2° and 26.9±0.2°.

In some embodiments, the crystal form A of the compound II in the present invention can be identified using differential scanning calorimetry. In some embodiments, the crystal form A has a differential scanning calorimetry pattern substantially as shown in 11. In the DSC pattern, the crystal form A has an endothermic peak at about 230.1~233.1° C. The results of differential scanning calorimetry are determined by DSC 200F3 240-20-0954-L from NETZSCH (purge gas: nitrogen; flow rate: 60 mL/min; heating rate: 10° C./min, assay range: 30° C.-300° C.).

In some embodiments, the crystal form A of the compound II in the present invention have an L-tartaric acid content of about 12.01% to 13.27%, which can be identified using ion chromatography, conductivity detection, and calculation of the major component content using an external standard method.

In some embodiments, the crystal form A of the compound II in the present invention can be identified by $^1$HNMR, the results of $^1$HNMR as follows: $^1$HNMR (500 MHz, CDCl$_3$) δ ppm: 1.01-1.04 (t, 3H, CH3, J=5.3 Hz), 1.50-1.52 (d, 3H, CH3, J=6.5 Hz), 1.93-1.95 (m, 2H, CH2), 2.03-2.06 (m, 1H, CH2), 2.16-2.19 (m, 1H, CH2), 2.50 (s, 8H, CH2), 2.57 (s, 2H, CH2), 2.93-3.09 (m, 2H, CH2), 3.47 (s, 1H, CH2), 4.02 (s, 1H, CH), 4.79 (s, 1H, CH), 7.68-7.70 (d, 1H, CH, J=10.5), 7.71-7.73 (d, 1H, Ar—H, J=12.5), 8.12 (s, 1H, Ar—H), 8.20 (s, 1H, Ar—H), 8.21 (s, 1H, Ar—H), 8.68-8.69 (d, 1H, Ar—H, J=3.5), 10.03 (s, 1H, N—H).

Preferably, the purity of the crystal form A≥85%.
Preferably, the purity of the crystal form A≥95%.
Preferably, the purity of the crystal form A≥99%.
Preferably, the purity of crystal form A≥99.5%.
Preferably, the crystal form A is an anhydrate.

The crystal form A of the compound II provided by the present invention has the characteristics of good crystallinity, weak hygroscopicity, and good stability, and has acceptable oral bioavailability.

Crystal Form B of Compound II

The present invention also provides another crystal form of the compound II, for convenience, which is referred as crystal form B in the present invention. The crystal form B approximately has an X-ray powder diffraction pattern as shown in FIG. 2.

Preferably, the purity of the crystal form B≥85%.
Preferably, the purity of the crystal form B≥95%.
Preferably, the purity of the crystal form B≥99%.
Preferably, the purity of the crystal form B≥99.5%.
Preferably, the crystal form B is an anhydrate.

Crystal Form of the Compound II

The present invention also provides another crystal form of the compound II, for convenience, which is referred as crystal form C in the present invention. The crystal form C approximately has an X-ray powder diffraction pattern as shown in FIG. 3.

Preferably, the purity of the crystal form C≥85%.
Preferably, the purity of the crystal form C≥95%.
Preferably, the purity of the crystal form C≥99%.
Preferably, the purity of the crystal form C≥99.5%.

The present invention provides an amorphous form of compound II or solvate thereof, the amorphous form approximately has an X-ray powder diffraction pattern as shown in FIG. 4.

The present invention also provides a pharmaceutical composition comprising a therapeutically effective amount of crystal form A, crystal form B and/or crystal form C of compound II.

The present invention additionally provides preferred embodiments of the pharmaceutical composition described above:

Preferably, the pharmaceutical composition comprise a therapeutically effective amount of crystal form A, crystal form B and/or crystal form C of compound II, and pharmaceutically acceptable excipients, auxiliaries or carriers.

Preferably, the pharmaceutical composition comprise a therapeutically effective amount of crystal form A of compound II, and pharmaceutically acceptable excipients, auxiliaries or carriers.

Preferably, the pharmaceutical composition comprise a therapeutically effective amount of crystal form A, crystal form B and/or crystal form C of compound II, and at least one other active ingredient.

Preferably, the pharmaceutical composition comprise a therapeutically effective amount of crystal form A of compound II, and at least one other active ingredient.

Preferably, the pharmaceutical composition is an oral formulation.

Preferably, the pharmaceutical composition is tablet or capsule.

The present invention also provides use of crystal form A, crystal form B and/or crystal form C of compound II in the manufacture of a medicament for the treatment of a disease, disorder or condition in a patient, wherein, the disease, disorder or condition is mediated by CDK, such as CDK4 and/or CDK6.

The present invention also provides preferred embodiments of crystal form A, crystal form B and/or crystal form C of the compound II.

Preferably, the disease, disorder or condition is a cancer and/or proliferative disease.

Preferably, the disease, disorder or condition is colon cancer, rectal cancer, mantle cell lymphoma, multiple myeloma, breast cancer, prostate cancer, glioblastoma, squamous cell esophageal cancer, liposarcoma, T-cell lymphoma, melanoma, pancreatic cancer, brain cancer or lung cancer.

Preferably, the disease, disorder or condition is breast cancer.

The present invention also provides a method of treating a disease, disorder, or condition in a patient by administering crystal form A, crystal form B and/or crystal form C of compound II to the patient.

The present invention further provides preferred embodiments of the method of treating a disease, disorder, or condition in a patient with crystal form A, crystal form Band/or crystal form C of compound II disease, disorder or condition:

Preferably, the disease, disorder or condition is mediated by CDK, such as CDK4 and/or CDK6.

Preferably, the disease, disorder or condition is a cancer and/or proliferative disease.

Preferably, the disease, disorder or condition is colon cancer, rectal cancer, mantle cell lymphoma, multiple myeloma, breast cancer, prostate cancer, glioblastoma, squamous cell esophageal cancer, liposarcoma, T-cell lymphoma, melanoma, pancreatic cancer, brain cancer or lung cancer.

Preferably, the disease, disorder or condition is breast cancer.

Crystal Form D of Compound III

The present invention provides a crystal form of compound III and/or solvate thereof, for convenience, the present invention is referred as crystal form D. The crystal form D approximately has an X-ray powder diffraction pattern as shown in FIG. 5.

Preferably, the purity of the crystal form D≥85%.
Preferably, the purity of the crystal form D≥95%.
Preferably, the purity of the crystal form D≥99%.
Preferably, the purity of the crystal form D≥99.5%.
Preferably, the crystal form D is an anhydrate.

Crystal Form E of Compound III

The present invention provides a crystal form of compound III and/or solvate thereof, for convenience, the present invention is referred as crystal form E. The crystal form E approximately has an X-ray powder diffraction pattern as shown in FIG. 6.

Preferably, the purity of the crystal form E≥85%.
Preferably, the purity of the crystal form E≥95%.
Preferably, the purity of the crystal form E≥99%.
Preferably, the purity of the crystal form E≥99.5%.
Preferably, the crystal form E is a dehydrate.

Crystal Form F of Compound III

The present invention provides a crystal form of compound III and/or solvate thereof, for convenience, the present invention is referred as crystal form F. The crystal form F approximately has an X-ray powder diffraction pattern as shown in FIG. 7.

Preferably, the purity of the crystal form F≥85%.
Preferably, the purity of the crystal form F≥95%.
Preferably, the purity of the crystal form F≥99%.
Preferably, the purity of the crystal form F≥99.5%.
Preferably, the crystal form F is a 1.5 hydrate.

Crystal Form G of Compound III

The present invention provides a crystal form compound III and/or solvate thereof, for convenience, the present invention is referred as crystal form G. The crystal form G approximately has an X-ray powder diffraction pattern as shown in FIG. 8.

Preferably, the purity of the crystal form G≥85%.
Preferably, the purity of the crystal form G≥95%.
Preferably, the purity of the crystal form G≥99%.
Preferably, the purity of the crystal form G≥99.5%.
Preferably, the crystal form G is a 2.5 hydrate.

The present invention also provides amorphous form compound III and/or solvate thereof, the amorphous form approximately has an X-ray powder diffraction pattern as shown in FIG. 9.

The present invention further provides a pharmaceutical composition comprising a therapeutically effective amount of crystal form D, crystal form E, crystal form F and/or crystal form G of compound III.

The present invention also provides preferred embodiments of the pharmaceutical composition:

Preferably, the pharmaceutical composition comprise a therapeutically effective amount of crystal form D, crystal form E, crystal form F and crystal form G of compound III, and pharmaceutically acceptable excipients, auxiliaries or carriers.

Preferably, the pharmaceutical composition comprises a therapeutically effective amount of crystal form D, crystal form E, crystal form F and crystal form G compound III, and at least another active ingredient.

Preferably, the pharmaceutical composition is an oral formulation.

Preferably, the pharmaceutical composition is a tablet or capsule.

The present invention also provides use of crystal form D, crystal form E, crystal form F and/or crystal form G of compound III in the manufacture of a medicament for the treatment of a disease, disorder or condition in a patient, wherein, the disease, disorder or condition is mediated by CDK, such as CDK4 and/or CDK6.

The present invention also provides preferred embodiments of use of crystal form D, crystal form E, crystal form F and/or crystal form G of compound III:

Preferably, the disease, disorder or condition is cancer and/or proliferative disease.

Preferably, the disease, disorder or condition is colon cancer, rectal cancer, mantle cell lymphoma, multiple myeloma, breast cancer, prostate cancer, glioblastoma, squamous cell esophageal cancer, liposarcoma, T-cell lymphoma, melanoma, pancreatic cancer, brain cancer or lung cancer.

Preferably, the disease, disorder or condition is breast cancer.

The present invention also provides a method of treating a disease, disorder, or condition in a patient by administering to the patient crystal form D, crystal form E, crystal form F and/or crystal form G of compound III.

The present invention further provides preferred embodiments of a method of treating a disease, disorder, or condition in a patient by administering to the patient crystal form D, crystal form E, crystal form F and/or crystal form G of compound III:

Preferably, the disease, disorder or condition is mediated by CDK, such as CDK4 and/or CDK6.

Preferably, the disease, disorder or condition is cancer and/or proliferative disease.

Preferably, the disease, disorder or condition is colon cancer, rectal cancer, mantle cell lymphoma, multiple myeloma, breast cancer, prostate cancer, glioblastoma, squamous cell esophageal cancer, liposarcoma, T-cell lymphoma, melanoma, pancreatic cancer, brain cancer or lung cancer.

Preferably, the disease, disorder or condition is breast cancer.

In some embodiments, the present invention provides a crystal form of the salt of compound I, the crystal form is prepared by following steps:

1) suspending (R)—N-(5-((4-ethylpiperazin-1-yl)methyl) pyridin-2-yl)-5-fluoro-4-(6-fluoro-1-methyl-1,2,3,4-tetrahydrobenzo[4,5]imidazo[1,2-a]pyrimidin-2-amine (compound I) in water and/or a water-soluble organic solvent, obtaining a suspension;
2) heating the suspension to 50° C. or more;
3) keeping the temperature at 50° C. or more, adding the acid to the suspension, and carrying out an acidification treatment, obtaining a clear solution;
4) cooling the clear solution to room temperature, filtering while stirring, drying the filter cake, obtaining the crystal form of salt of compound I.

Such as, the acid is L-tartaric acid in the step 3), the crystal form in step 4) is the crystal form of L-tartaric acid salt of the compound I.

Such as, the acid is methanesulfonic acid in the step 3), the crystal form in step 4) is the crystal form of methanesulfonic acid of the compound I.

In some embodiments, the crystal form A of the compound II is prepared by following steps:
Dissolving the compound I in methanol at 50-70° C. to obtain a clear solution, dissolving L-tartaric acid in methanol, adding the solution of L-tartaric acid in methanol dropwise to the solution of compound I in methanol, filtering after stirring, drying a filter cake at 40-70° C., obtaining the crystal form A of the compound II.

In some embodiments, a method for preparing the crystal form B of the compound II, comprising:
Adding water and acetone to the crystal form A of the compound II, obtaining a clear solution, stirring after filtering, then stirring at 0-20° C., precipitating solid, drying after centrifuging, obtaining the crystal form B of the compound II.

In some embodiments, a method for preparing the crystal form C of the compound II, comprising:
Under stirring, 1-03 (100 g), anhydrous methanol (1 L) are added to 2 L reaction kettle sequently, heated to 65° C. After the reaction mixture is clarified for 0.5 h, a solution of L-tartaric acid in methanol (a solution of 30.09 g tartaric acid in 100 mL anhydrous methanol) is added dropwise. The dropping time is controlled for 45-60 min. After the dropping is completed, the solution is reacted at 65° C. for 4 h. Then a solution of L-tartaric acid in methanol (a solution of 7.48 g tartaric acid in 100 mL anhydrous methanol) is added. The dropping time is controlled for 30-45 min. After the dropping is completed, the solution is reacted at 65° C. for 1.5 h. Then a solution of L-tartaric acid in methanol (a solution of 8.55 g tartaric acid in 100 mL anhydrous methanol) is added. The dropping time is controlled for 30-45 min. After the dropping is completed, the solution is reacted at 65° C. for 1.5 h. The solution is cooled to below 10° C., filtered, the filter cake is washed with methanol (100 mL×2), then dried in vacuum at 45° C. for 36 h, 109.4 g of light yellow crystal power is obtained, which is the L-tartaric acid salt of the compound II. The powder is identified by X ray powder diffraction. The result shows that the crystal form is crystal form C of L-tartaric acid salt of the compound II.

In some embodiments, a method of preparing the amorphous form of the compound II, comprising:
Trifluoroethanol is added to the crystal form A of compound II, the clear solution is obtained, then the clear solution is concentrated under reduced pressure, and the amorphous form of compound II is obtained.

The amorphous form of Compound II readily forms Form B of Compound II under the influence of moisture in a room temperature environment.

The amorphous form of compound II is readily converted to the crystal form B of compound II under the influence of water at room temperature.

Exemplarily, the present invention also provides a method of preparing L-tartaric acid salt (compound II) of (R)—N-(5-((4-ethylpiperazin-1-yl)methyl)pyridin-2-yl)-5-fluoro-4-(6-fluoro-1-methyl-1,2,3,4-tetrahydrobenzo[4,5]imidazo[1,2-a]pyridin-8-yl)pyrimidin-2-amine, comprising:

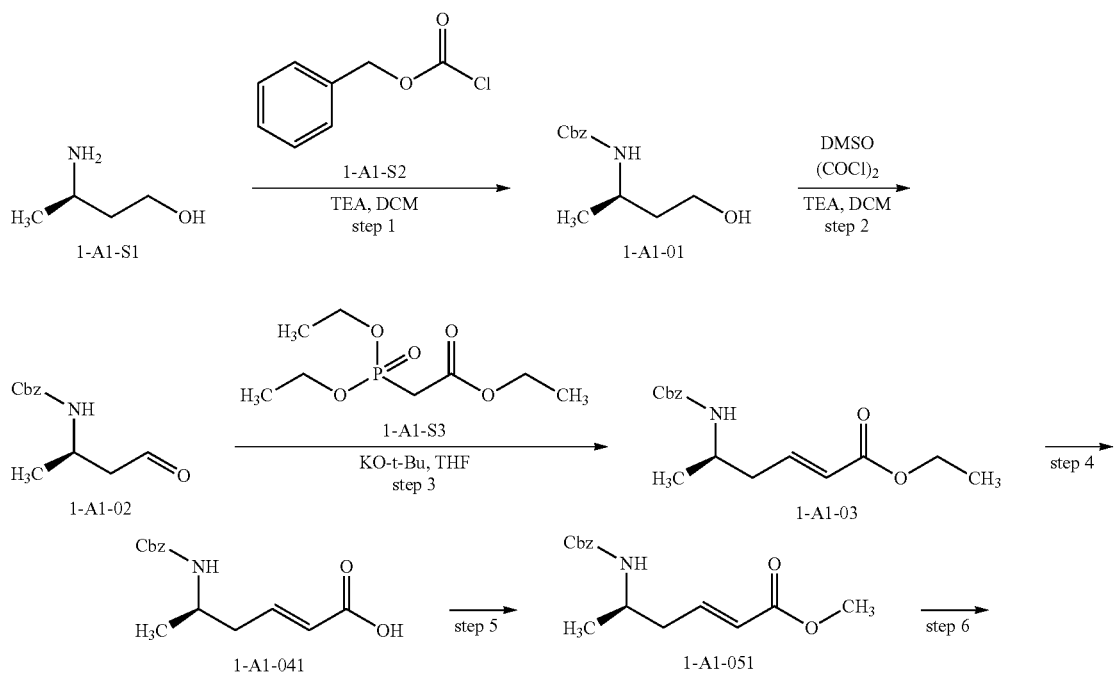

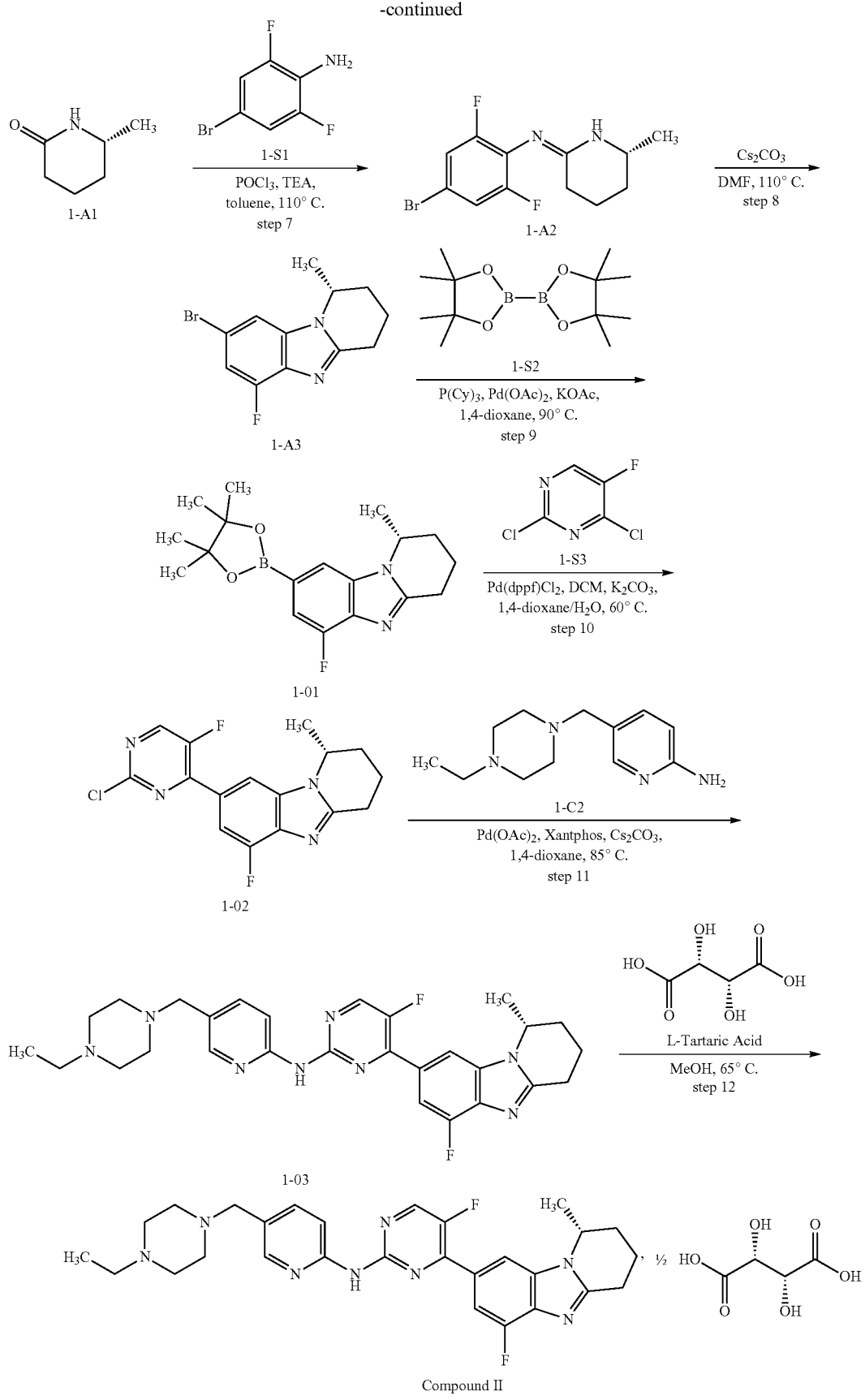

In some embodiments, a method of preparing the crystal form D of compound III, comprising:

Compound I is dissolved in methanol at 50-70° C., methanesulfonic acid is dissolved in methanol. The solution of methanesulfonic acid in methanol is dropwise added to the solution of compound I. After stirring, isopropyl ether is dropwise added, a solid is slowly precipitated, filtered, the filter cake is dried at 40-70° C., a solid is obtained. Isopropyl ether is dropwise added to mother liquor, filtered after stirring, the filter cake is dried at 40-70° C., a solid is obtained. The solid obtained above is continuously dried, the crystal form D of compound III is obtained.

In some embodiments, the method of preparing the crystal form E of compound III, comprising:

The crystal form D of compound III is placed at room temperature under 52% RH humidity for 1-4 days, the crystal form E of compound III is obtained.

In some embodiments, the method of preparing the crystal form F of compound III, comprising:

The crystal form E of compound III is placed at room temperature under 44% RH humidity for 1-14 days, the crystal form F of compound III is obtained.

In some embodiments, the method of preparing the crystal form G of compound III, comprising:

The crystal form D of compound III is placed at room temperature under 97% RH humidity for 1-4 days, the crystal form G of compound III is obtained.

In some embodiments, the method of preparing the amorphous form of compound III, comprising:

The crystal form D of compound III is dissolved in water, then the mixture was concentrated under reduced pressure, a viscous solid is obtained, which is the amorphous form of compound III.

The amorphous form of compound III is unstable when scaled up to 50 mg, which converts to a crystal form.

All crystal forms of the invention are substantially pure.

The term "substantially pure" as used herein means that at least 85% by weight, preferably at least 95% by weight, more preferably at least 99% by weight, most preferably at least 99.5% by weight of the crystal form in the compound of formula I present in the present invention, especially in form A, form B and/or form C.

As described herein, new crystal forms can be identified by X-ray powder diffraction pattern, however, those skilled in the art will recognize that the peak intensities and/or peak conditions of X-ray powder diffraction may vary from experimental condition to experimental condition, such as different diffraction test conditions and/or preferential orientation, etc. At the same time, the measured value of $2\theta$ will have an error of about ±0.2° due to the different accuracy of the different instruments. However, it is known that the relative intensity value of the peak is more dependent than the position of the peak on certain properties of the sample being measured, such as the size of the crystals in the sample, the orientation of the crystals and the purity of the material being analyzed. It is therefore possible to show peak intensity deviations in the range of about ±20% or more. However, in spite of experimental error, instrumental error and orientation preference, one skilled in the art can also obtain sufficient information to identify the crystal form from the XRD data provided in this patent.

In the present invention, "having an X-ray powder diffraction pattern as shown in FIG. 1" or "having an X-ray powder diffraction pattern as shown in FIG. 2" means that the X-ray powder diffraction pattern shows a major peak as shown in FIG. 1 or FIG. 2, wherein the major peak is compared to the highest peak in FIG. 1 or FIG. 2 whose relative intensity is designated as 100%. Those peaks having relative intensity values in excess of 10%, preferably in excess of 30%.

In the present invention, reference to "adding methanol/acetone" and the like in the method of preparing the crystal form means that methanol is added first and then acetone is added, and similarly, "ethanol/water" means that ethanol is added first and then water is added; additionally, "trifluoroethanol/ethyl acetate" means that trifluoroethanol is added first and then ethyl acetate is added. Similarly, for example, "solvent 1/solvent 2" means that solvent 1 is added first and then solvent 2 is added; by "solvent 2/solvent 1" is meant that solvent 2 is added first followed by solvent 1.

In the present invention, the term "therapeutically effective amount" refers to an amount of a compound/crystal form, when administered to a subject, is sufficient to effect such treatment of a disease, disorder, or symptom in the treatment of a disease, or at least one clinical symptom of a disease or disorder. "Therapeutically effective amount" can vary with the compound, disease, disorder, and/or symptom of the disease or disorder, the severity of the disease, disorder, and/or symptom of the disease or disorder, the age of the patient being treated, and/or the weight of the patient being treated, etc. any particular case, an appropriate amount will be apparent to those skilled in the art. It may also be determined by routine experimentation. "Therapeutically effective amount" in the case of combination therapy refers to the total amount of the combination subject effective to treat the disease, disorder or condition.

All dosage forms of the pharmaceutical compositions of the present invention may be prepared by conventional methods in the pharmaceutical art, for example, by mixing the active ingredient with one or more accessory ingredients and then preparing the desired dosage form.

"Pharmaceutically acceptable carrier" refers to a conventional pharmaceutical carrier suitable for the desired pharmaceutical formulation, for example: diluents, excipients such as water, various organic solvents, and the like; fillers such as starch, sucrose and the like; Binders such as cellulose derivatives, alginates, gelatin and polyvinylpyrrolidone (PVP); humectants such as glycerol; disintegrants such as agar-agar, calcium carbonate and sodium bicarbonate; absorption promoters such as quaternary ammonium compounds; a surfactant such as cetyl alcohol; Absorbent carriers such as kaolin and bentonite; lubricants, such as talc, calcium stearate, magnesium stearate, polyethylene glycol, and the like, may additionally be added to the pharmaceutical compositions with other pharmaceutically acceptable adjuvants, such as dispersing agents, stabilizing agents, thickening agents, complexing agents, buffering agents, penetration enhancers, polymers, flavoring agents, sweetening agents, and dyes. Adjuvants appropriate to the desired dosage form and the desired mode of administration are preferably employed.

The term "disease, disorder", or "condition" refers to any disease, disorder, disease, symptom, or indication.

EXAMPLES

Figure 1:
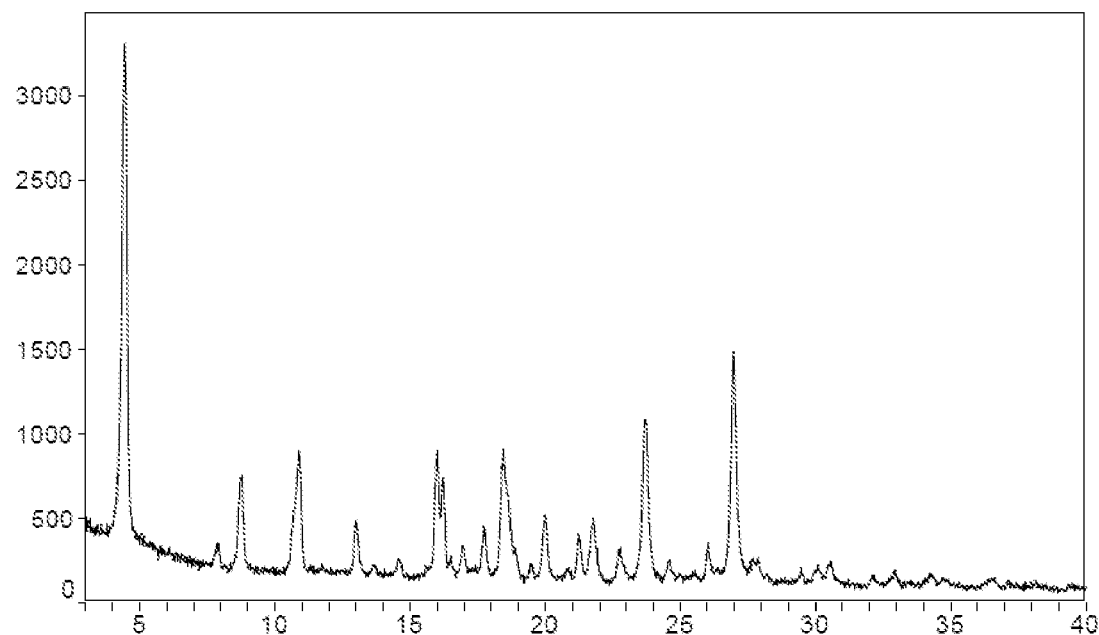
FIG. 1: XRD pattern of crystal form A of compound II (small sample, batch number: 1072P04-A14S01).
Figure 2:
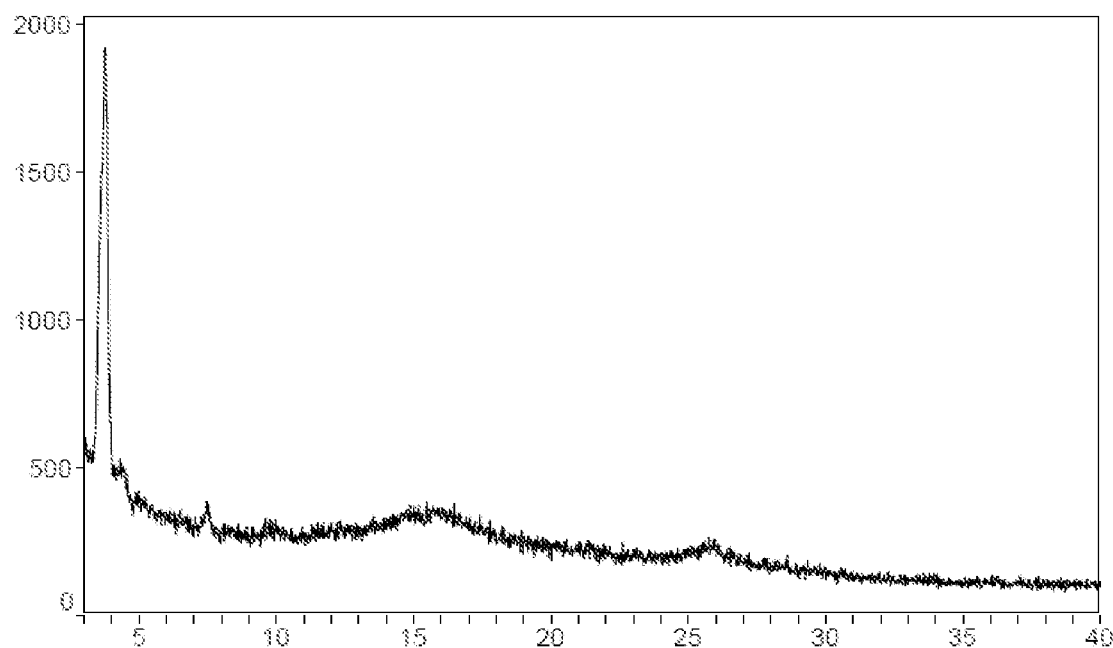
FIG. 2: XRD pattern of crystal form B.
Figure 3:
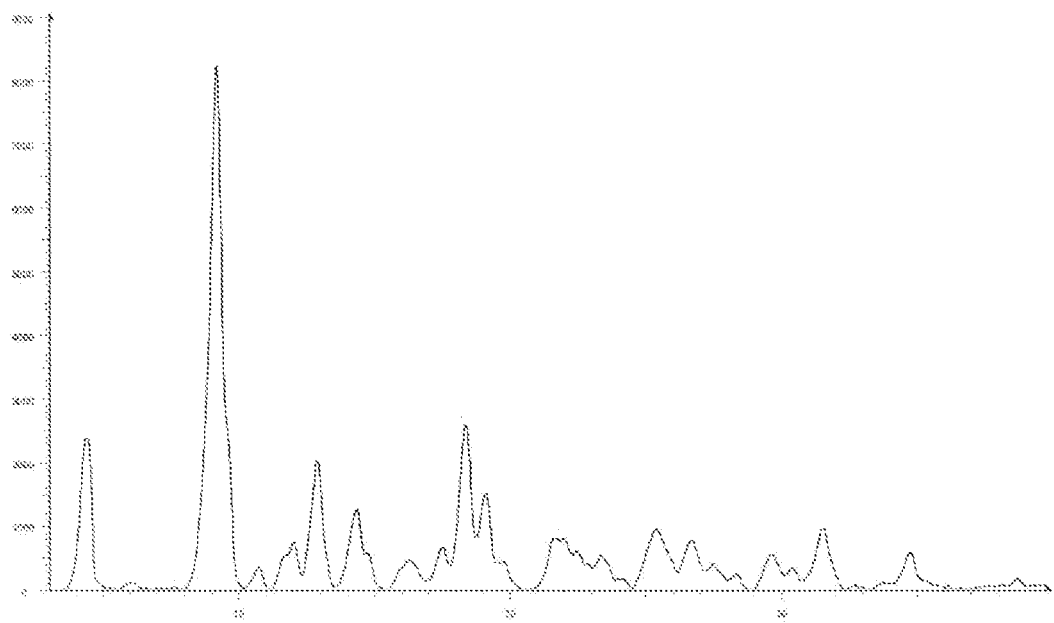
FIG. 3: XRD pattern of crystal form C of compound II.
Figure 4:
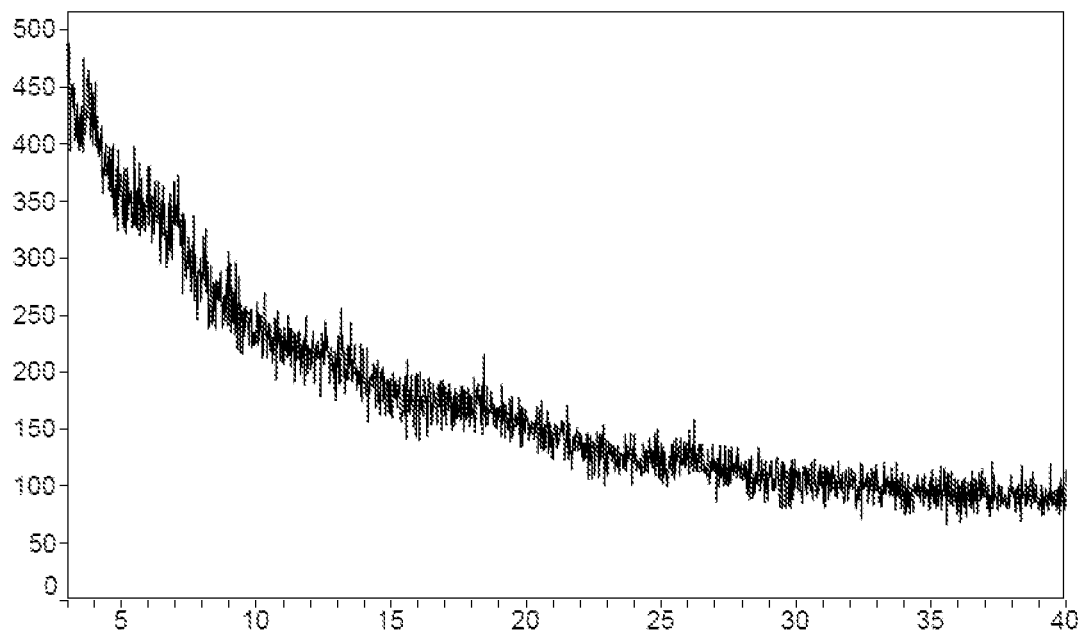
FIG. 4: XRD pattern of amorphous form of compound II.
Figure 5:
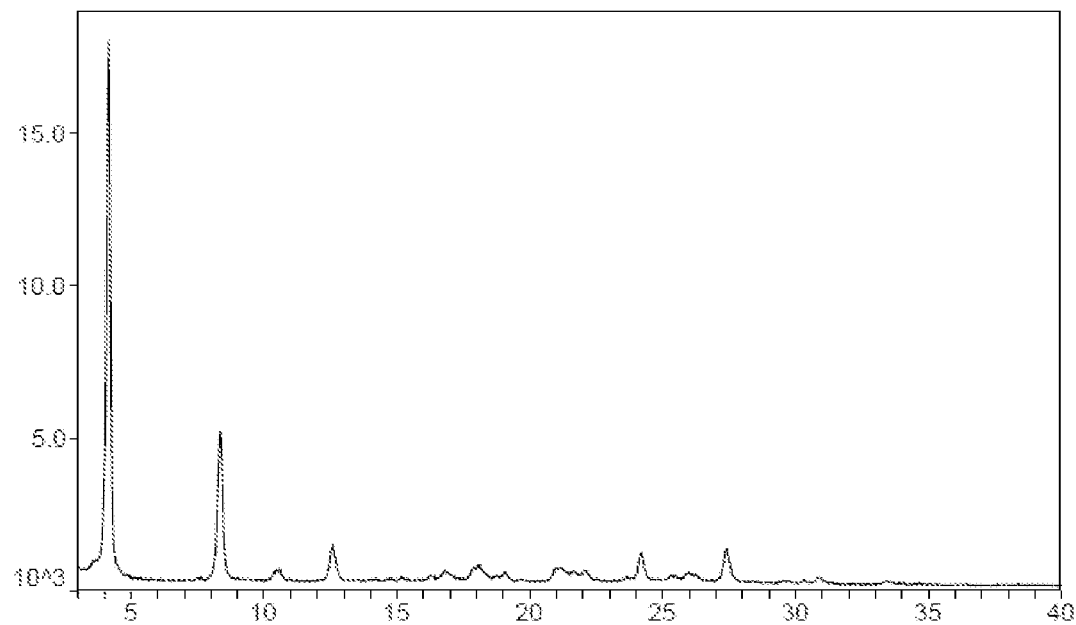
FIG. 5: XRD pattern of crystal form D of compound III.
Figure 6:
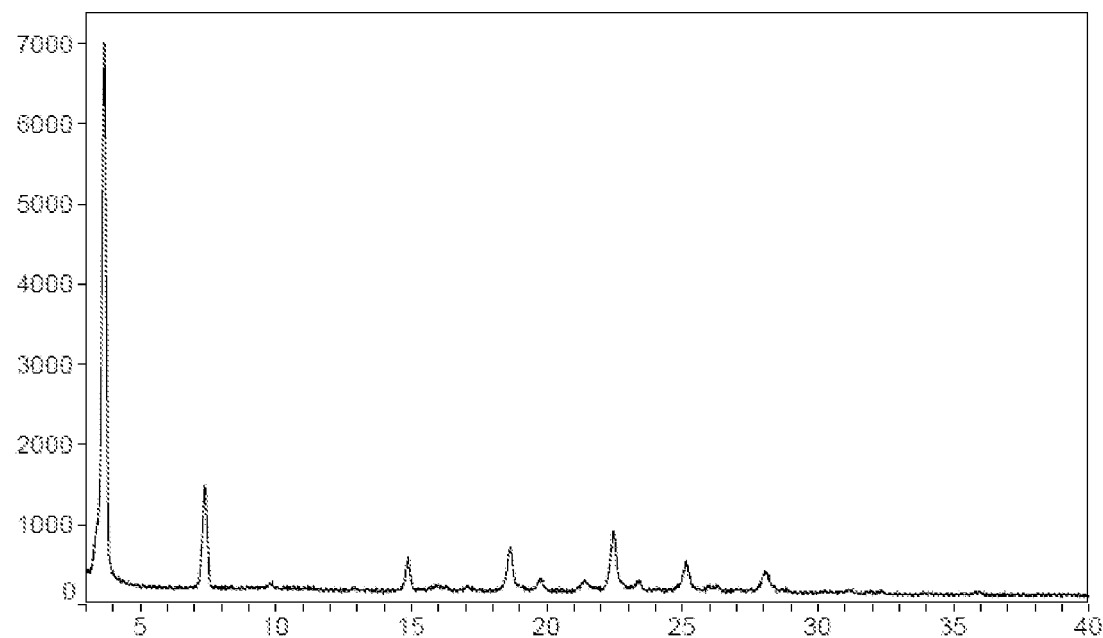
FIG. 6: XRD pattern of crystal form E of compound III.
Figure 7:
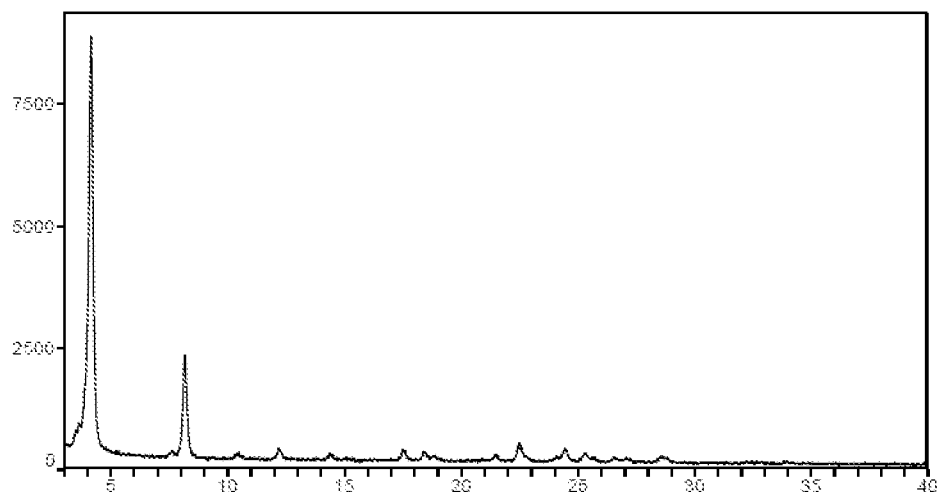
FIG. 7: XRD pattern of crystal form F of compound III.
Figure 8:
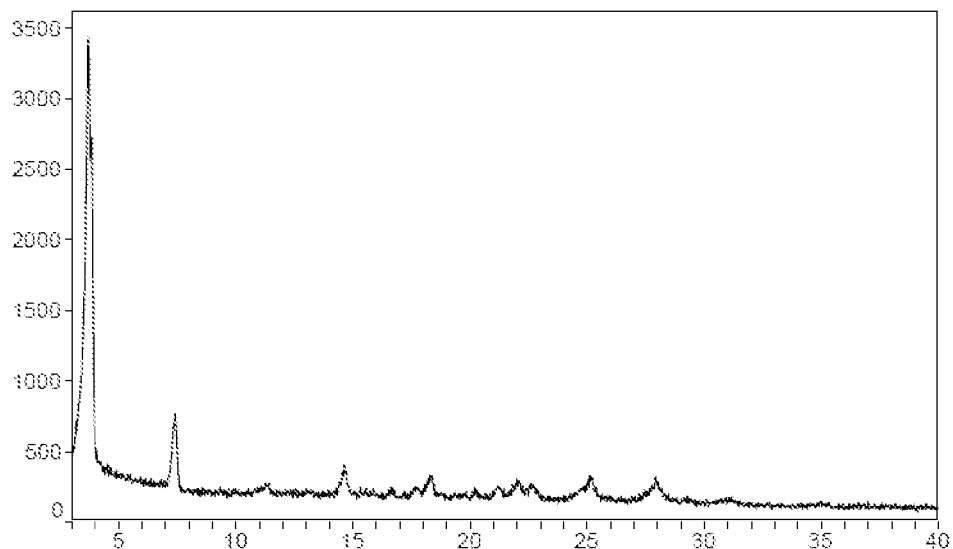
FIG. 8: XRD pattern of crystal form G of compound III.
Figure 9:
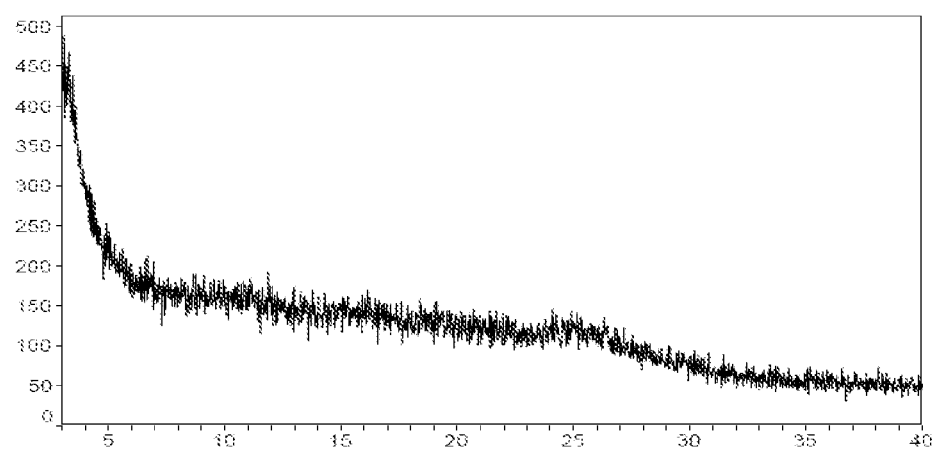
FIG. 9: XRD pattern of amorphous form of compound III.

The present invention will be further illustrated by the following examples, but it should not be construed that the present invention is confined to the scope of the examples. In the techniques or methods of the following examples, where the specific conditions were not specifically described, they could be selected from conventional methods and conditions.

Abbreviations

Cbz-Cl: Benzyl chloroformate;
DCM: Dichloromethane;
DMF: N, N-Dimethylformamide;
DMSO: Dimethyl sulfoxide;
DSC: Differential scanning calorimetry;
DVS: Dynamic vapor adsorption;
EtOH: Ethanol;
EtOAc: Ethyl acetate;
KOAc: Acetic acid potassium;
KO-t-Bu: Potassium tert-butoxide;
MeOH: methanol;
P(Cy)$_3$: Tricyclohexylphosphine;
Pd(OAc)$_2$: Palladium acetate;
Pd(dppf)Cl$_2$: [1,1'-Bis(diphenylphosphino)ferrocene] palladium dichloride;
RT: room temperature;
RH: Relative humidity;
TGA: Thermogravimetric analysis;
TEA: Triethanolamine;
THF: Tetrahydrofuran;
Xantphos: 4,5-bis(diphenylphosphino)-9, 9-dimethylxanthene;
XRD: X-ray powder diffraction pattern.

Example 1 Synthesis of Crystal Form A of Compound II

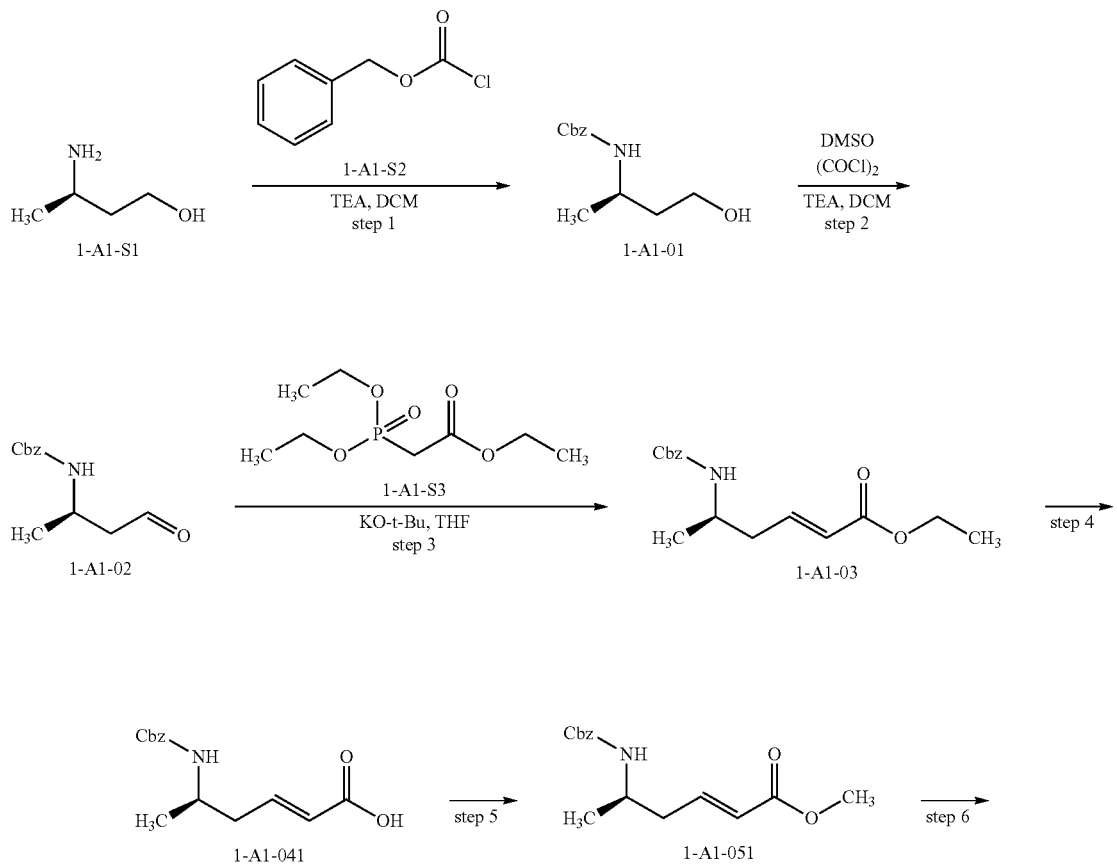

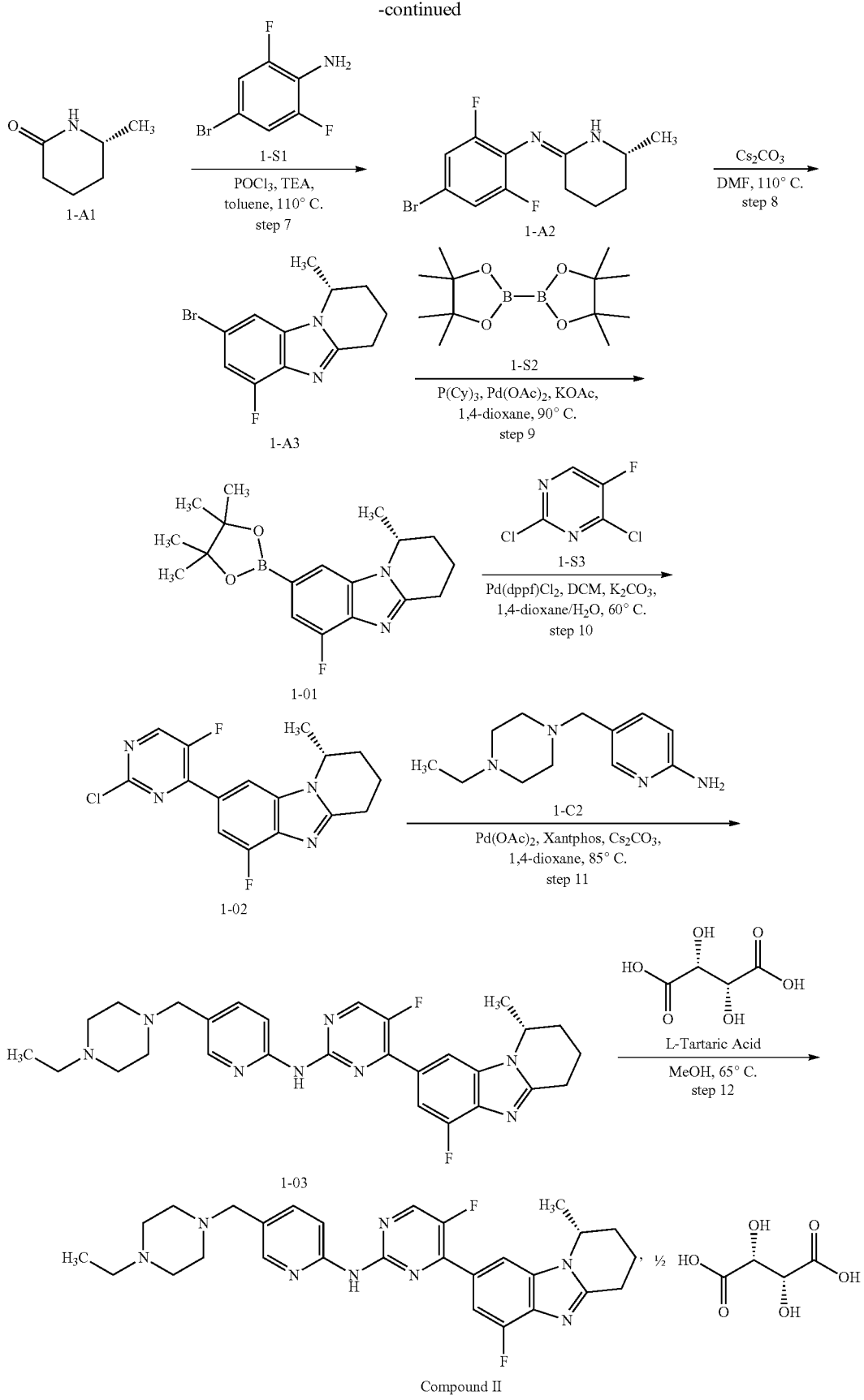

Synthesis of 1-A1-01 (Step 1)

DCM (20 L), 1-A1-S1 (300 g) and Et₃N (390 g) was added to 50 L reaction kettle, and cooled to below −5° C., then to the mixture above was dropwise added Cbz-Cl (570 g) for 5. After the dropping is completed, the reaction mixture was warmed to room temperature and reacted, TLC (EtOAc:hexane=1:3) monitored until the reaction was completed. To the reaction mixture was added water (1.5 L), then concentrated hydrochloric acid (80 mL) was slowly dropwise added, pH was adjusted to 1-2. The organic phase was separated and then washed with 15 L of water, dried over anhydrous $Na_2SO_4$ for 0.5 h, filtered to remove the drying agent, the filtrate was collected and concentrated. 730 g of 1-A1-01 (crude) was obtained as light yellow oily liquid in 95.4% yield.

Synthesis of 1-A1-02 (Step 2)

To a 20 L reaction flask was added 720 mL of DCM, DMSO (90 g), the mixture was stirred and cooled to below −65° C. under nitrogen, then $COCl_2$ was dropwise added for 2 h. After the dropping is completed, the mixture was stirred for 20 min below −65° C.; then a solution of 1-A1-01 in DCM (143 g/500 mL DCM) was dropwise added for 40 min. After the dropping is completed, the mixture was reacted for 15 min below −65° C. Below −65° C., to the mixture was dropwise added TEA for 2 h. After the dropping is completed, the reaction mixture was warmed to −20° C., then 250 L water was added, pH was adjusted to 1-2 with HCl. The organic phase was separated and then washed with water (1 L×2), dried over anhydrous $Na_2SO_4$, filtered to remove the drying agent, the filtrate was collected and concentrated. 432 g of crude 1-A1-02 was obtained as yellow oily liquid. The crude produce was directly used in the next step.

Synthesis of 1-A1-03 (Step 3)

400 mL THF, KOt-Bu (215 g) was added to 1 L reaction kettle, and cooled to 5-15° C., to the mixture was dropwise added triethyl phosphonoacetate (430 g) for 50 min. After the dropping is completed. A solution of 1-A1-02 in THF (431 g/100 mL THF) was dropwise for 1 h below 15° C. After the dropping is completed, TLC (EtOAc:hexane=1:3) monitored until the reaction was completed. To the reaction mixture was added saturated NaCl (1.5 L), THF phase was collected. The water phase was exacted with DCM (2 L), then the organic phase was dried over anhydrous $Na_2SO_4$ for 0.5 h, filtered to remove the drying agent, the filtrate was collected and concentrated. The residue was purified by column chromatography. 390 g of 1-A1-03 was obtained as light yellow oily liquid.

Synthesis of 1-A1-041 (Step 4)

Aqueous NaOH solution (301 g NaOH/1.5 L water) was added to a solution of 1-A1-03 in THF (601 g/2.3 L THF), and heated to reflux for 3-4 h in a 5 L reaction kettle. The resulting mixture was cooled to 40-50° C., stranded and separated, the organic phase (THF) was collected and concentrated to give a solid. The solid was dissolved in water (20 L), the water phase was extracted with methyl tertiary butyl ether (2 L), EtOAc (2 L), methyl tertiary butyl ether (2 L) sequently. Then the water phase was adjusted pH to 1-2 with concentrated HCl, and extracted with EtOAc (1.5 L, 3 L) for two times. The organic phase was combined, and dried over anhydrous $Na_2SO_4$ for 0.5 h, filtered to remove the drying agent, the filtrate was collected and concentrated to give a solid. The solid was slurried with isopropyl ether (3 L) for 2 h, filtered to give a solid. The solid was washed with isopropyl ether (1 L). The solid is dried for 3-4 h at 50° C. by air blowing. 331 g of 1-A1-041 was obtained as a light yellow solid in 52.7% yield.

Synthesis of 1-051 (Step 5)

1-A1-041 (600 g), methanol (25 L), concentrated $H_2SO_4$ was added to 50 L reaction kettle, and heated to reflux for 3-4 h. After the reaction is finished, the reaction mixture was cooled to room temperature. Then the mixture was concentrated, to the residue obtained was added DCM (15 L), then the mixture was adjusted to pH=9-10 with $K_2CO_3$. The organic phase was collected, dried over anhydrous $Na_2SO_4$ for 0.5 h, filtered to remove the drying agent, the filtrate was collected and concentrated. 6.37 kg of 1-A1-051 was obtained as a white-off solid in 97.3% yield.

Synthesis of 1-A1 (Step 6)

1-A1-051 (500 g), methanol (1.8 L) and Pd/C was added to a 2 L reaction kettle, the system was replaced air with nitrogen, and replaced nitrogen with hydrogen for three times in turn. The mixture was heated to 85° C., and reacted at 3.0 Mpa under hydrogen atmosphere for 3 h. The resulting mixture was cooled to room temperature, filtered to remove Pd/C, collected the organic phase, and the organic phase was concentrated to give a light yellow solid. To the solid was added isopropyl ether (3 L) and crystallized at −20° C. for 1 h, filtered to give a solid, the solid was washed with isopropyl ether (500 mL). 234 g of 1-A1 was obtained as a light yellow solid in 90.5% yield.

Synthesis of 1-A2 (Step 7)

$POCl_3$ (413 g) was dropwise added to a mixture of 1-A1 (200 g) and 4-bromo-2,6-difluroaniline (410 g) toluene (1.2 L) in 50 L reaction kettle for 1 h. After the dropping is completed, Et₃N was dropwise added in an ice bath for 1 h. After the dropping is completed, the mixture was heated to 110° C. and reacted for 1 h. Then the reaction mixture was cooled to 2-10° C., 1 L water was added, and the mixture was adjusted to pH=9-10 with saturated $K_2CO_3$, and extracted with EtOAc (1.5 L, 1 L) for two times, combined the organic phase. Then the organic phase was extracted with 2 L saturated NaCl, and dried over anhydrous $Na_2SO_4$ for 0.5 h, filtered to remove the drying agent, the filtrate was collected and concentrated to give a solid. The solid was slurried with isopropyl ether (1 L) for 10 min, filtered. 460 g of 1-A2 was obtained as a yellow solid.

Synthesis of 1-A3 (Step 8)

A mixture of 1-A2 (450 g), DMF (2 L), $Cs_2CO_3$ (700 g) was stirred at 110° C. for 24 h in a reaction kettle. TLC monitored until the reaction was completed. To the resulting mixture was added EtOAc (3 L), filtered to remove solid impurities, the filtrate was extracted with saturated NaCl (1 L×5), and the organic phase was dried over anhydrous $Na_2SO_4$ for 0.5 h, concentrated to give a solid, then the solid was slurried with methyl tertiary butyl ether (1 L×2) for 30 min, filtered. 382 g of 1-A3 was obtained as a light yellow solid in 90.10% yield.

Synthesis of 1-01 (Step 9)

1-A3 (380 g), Bis(pinacolato)diboron (400 g), KOAc (340 g), $Pd(OAc)_2$ (6 g), $P(Cy)_3$ (7 g), 1,4-dioxane was added to a reaction kettle, the mixture was heated to 90° C. and reacted for 2 h under nitrogen. TLC monitored until the reaction was completed. The resulting mixture was cooled to room temperature, filtered, the filtrate was concentrated to remove 1,4-dioxane, the residue was purified by column chromatography within-hexane and DCM, then the resulting product was slurried with n-hexane (1.2 L) for 1 h. 334 g of 1-01 was obtained as a rey solid in 70.10% yield.

Synthesis of 1-02 (Step 10)

A mixture of 1-01 (128 g), 1,4-dioxane (1 L), 1-S3 (85 g), $K_2CO_3$ (110 g), $Pd(dppf)Cl_2 \cdot DCM$ was heated to 60° C. and reacted for 4 h under nitrogen in a 2 L three-neck bottle. The reaction mixture was cooled to room temperature, and concentrated under reduced pressure to remove 1,4-dioxane. To the residue was added DCM (1.5 L) and water (1.1 L), stirred, stranded and separated. The water phase was extracted with DCM (10 L). The combined organic phase was extracted with 0.5% HCl (1 L×2), and saturated NaCl sequently. The organic phase was dried over anhydrous $Na_2SO_4$ (500 g), filtered to remove the drying agent, the filtrate was concentrated under reduced pressure. To the residue was added EtOAc (0.5 L) and stirred for 30 min to precipitate a solid, filtered. The solid was washed with EtOAc (0.5 L), then dried at 45° C. for 3 h in vacuum, a yellow solid (120 g) was obtained.

Synthesis of 1-03 (Step 11)

A mixture of 1-02 (100 g), 1,4-dioxane (1 L), 1-C2 (80 g), $Cs_2CO_3$ (163 g), $Pd(OAc)_2$ (2 g) and 4,5-bis(diphenylphosphino)-9,9-dimethylxanthene (Xantphos) (4 g) was stirred at 85° C. in 2 L three-neck bottle under nitrogen. After the reaction is finished, the resulting solution was cooled to room temperature, filtered to give a solid, the solid was washed with EtOAc. Then the solid was added to a mixture of DCM (1.5 L) and water (1.1 L), stirred, stranded, and the organic layer was separated out. Then the water phase was extracted with DCM (700 mL). And the organic phase was combined, then was washed with water (700 mL×2). The organic phase was dried over anhydrous $Na_2SO_4$ (700 g). $Na_2SO_4$ was removed by filtration, the filtrate was concentrated. To the residue was added methanol (0.5 L) and heated to 55-65° C. for 0.5 h, then cooled to room temperature, filtered to give a solid, the solid was washed with EtOAc 500 mL. The solid was dried at 45° C. under vacuum for 8 h. 111.79 g of 1-03 was obtained as a light yellow solid.

Synthesis of Compound II (Step 12)

1-03 (500 g), anhydrous methanol (3.8 L) was added to 10 L reaction kettle and heated to 65° C. After the mixture was stirred to a clear solution for 0.5 h, a solution of L-tartaric acid in methanol (150.89 g tartaric acid was dissolved in 500 mL anhydrous methanol) was dropwise added. The dropping time is controlled in range of 45-60 min. After the dropping is completed, the mixture was stirred at 65° C. for 4 h, a solution of L-tartaric acid in methanol (35.58 g tartaric acid was dissolved in 250 mL anhydrous methanol) was continuously dropwise added. The dropping time is controlled in range of 30-45 min. After the dropping is completed, the mixture was stirred at 65° C. for another 1 h, a solution of L-tartaric acid in methanol (36.55 g tartaric acid was dissolved in 250 mL anhydrous methanol) was continuously dropwise added. The dropping time is controlled in range of 30-45 min. After the dropping is completed, the mixture was stirred at 65° C. for another 1.5 h. The mixture was cooled to 20-30° C., filtered, the filter cake was washed with methanol (400 mL×2), then dried at 45° C. for 36 h in vacuum. 530.64 g of compound II was obtained as a light yellow crystal power. It showed that the crystal form was the crystal form A of compound II by X ray powder diffraction.

Example 2 the Detection Result of XRD

A small sample of compound II (batch number: 1072 P 04-A 14 S 01) and a pilot sample of compound II (batch number: 20170903) was synthesized according to the method of example 1, then the small sample and the pilot sample was then characterized by XRD.

In one embodiment of the invention, XRD analysis of the small sample (batch number: 1072P04-A14S01) was performed by SoliPharmausing Bruker D8 Advance Diffractometer. The detection instruments and detection parameters were showed in table 1, the data of XRD pattern was shown in table 2.

TABLE 1

XRD detection instruments and detection parameters of the small sample

| device | X-ray powder diffraction (XRD) & Heating stage XRD | |
|---|---|---|
| instruments | Bruker D8 Advance diffractometer | |
| Technical index | copper target wavelength: Kα = 1.54Å radiation (40 kV, 40 mA), θ-2θ goniometer, Mo monochromator, Lynxeye detector | |
| Calibration material | $Al_2O_3$ | |
| Acquisition software | Diffrac Plus XRD Commander | |
| Analysis software | MDI Jade 6 | |
| method parameter | specification of no reflection sample plate | 24.6 mm diameter × 1.0 mm thickness |
| | Variable temperature heating table sample plate | copper plate |
| | Angle of detection | 3~40° |
| | Step length | 0.02°/step |
| | speed | 0.2 s/step |

TABLE 2

XRD data of the small sample

| peak# | 2θ(°) | Relative intensity (I %) |
|---|---|---|
| 1 | 4.4 | 100.0 |
| 2 | 8.8 | 19.3 |
| 3 | 10.9 | 24.3 |
| 4 | 16.0 | 25.1 |
| 5 | 18.5 | 25.4 |
| 6 | 23.7 | 32.0 |
| 7 | 27.0 | 44.5 |

In another embodiment, XRD analysis of the pilot sample (batch number: 20170903) was performed by Beijing Center for Physical & Chemical Analysis using D8-Advance X radiation diffractometer, the reference method was JY/T 009-1996 «General rules for X-ray polycrystalline diffractometry». The detection instrument and detection parameter were showed in table 3, the data of XRD pattern was shown in table 4.

TABLE 3

XRD detection instruments and detection parameters of the pilot sample

| instruments technical indicator | D8-Advance X radiation diffractometer copper target wavelength: 1.5406 nm operating voltage: 40 kV operating current: 40 mA |
|---|---|
| experiment condition | 2θ scanned area 3~40° Step length 0.02°/step Residence time 0.1 s/step |

TABLE 4

XRD data of the pilot sample

| peak# | 2θ(°) | Relative intensity (I %) |
|---|---|---|
| 1 | 4.4 | 100.0 |
| 2 | 8.7 | 20.9 |
| 3 | 10.8 | 19.8 |
| 4 | 15.9 | 14.0 |
| 5 | 18.4 | 17.5 |

TABLE 4-continued

XRD data of the pilot sample

| peak# | 2θ(°) | Relative intensity (I %) |
|---|---|---|
| 6 | 23.6 | 22.6 |
| 7 | 26.9 | 34.6 |

Figure 12:
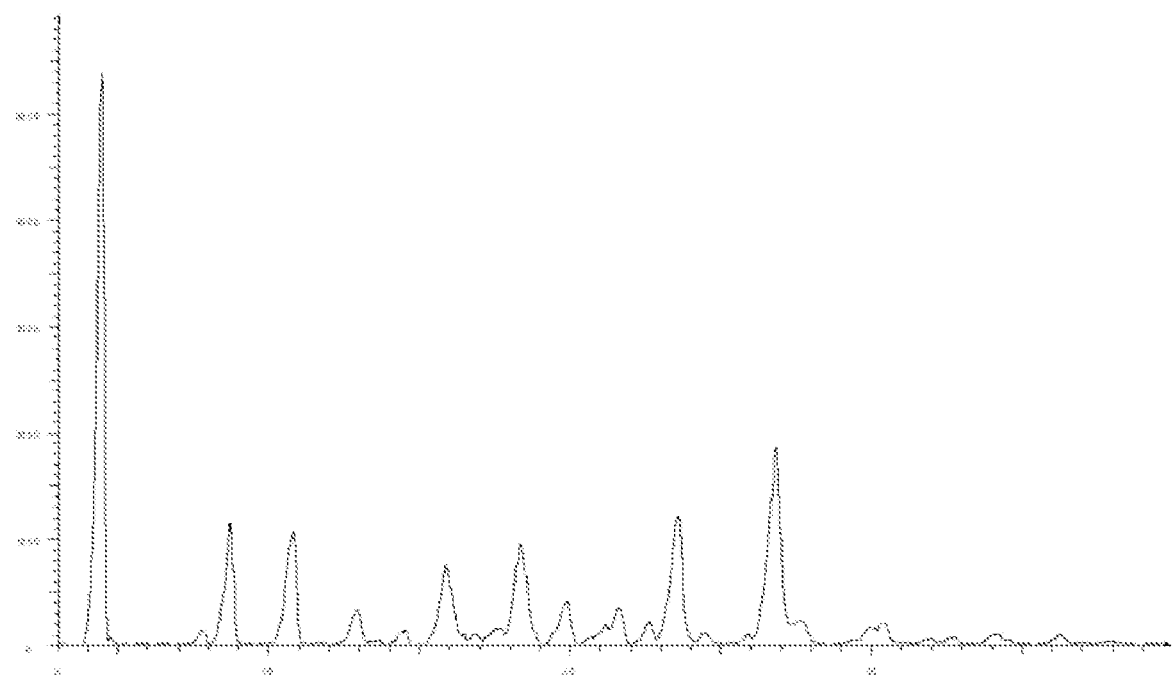
FIG. 12: XRD pattern of crystal form A of compound II (the pilot sample, batch number: 20170903).
In the above FIG. 1-FIG. 10 and FIG. 12, the abscissas (X-axis) represent the diffraction angle 2 θ in units of "°"; the ordinates (Y-axis) represent the diffraction intensity in unit of "counts".

It will be appreciated by those skilled in the art that during the acquisition of XRD patterns, the relevant data may be subjected to appropriate scientific processing, such as baseline correction processing, to reduce errors. It will also be appreciated by those skilled in the art that there may be some variation in the 2θ angle or degree of separation, etc., of the resulting XRD pattern when operated under different laboratory conditions. It is to be understood that the XRD pattern of the crystal form A of Compound II provided by the present invention is not limited to the X-ray powder diffraction pattern shown in FIG. 1 or FIG. 12, and crystals having substantially the same X-ray powder diffraction pattern as shown in FIG. 1 or FIG. 12 are within the scope of the present invention.

Example 3 the Stability of the Crystal Form

The detection instruments and methods of X-ray powder diffraction pattern in the present invention and was shown in table 1. The crystal form A of compound II, the crystal form D of compound III and the crystal form F of compound III was dried at 80° C. for 24 h, or 25° C., 60% RH for 10 days, or 40° C., 75% RH for 10 days, and XRD pattern shown in FIG. 10, the result was showed in table 5.

TABLE 5

Stability test results of different crystal forms of compound II

| crystal form of the compound | 80° C., 24 h | 25° C., 60% RH, 10 days | 40° C., 75% RH, is placed 10 days |
|---|---|---|---|
| crystal form A of the compound II | XRD unchanged | XRD unchanged | XRD unchanged |
| crystal form D of the compound III | XRD unchanged | XRD changed | XRD changed |
| crystal form F the compound III | XRD changed | XRD changed | XRD changed |

Figure 10:
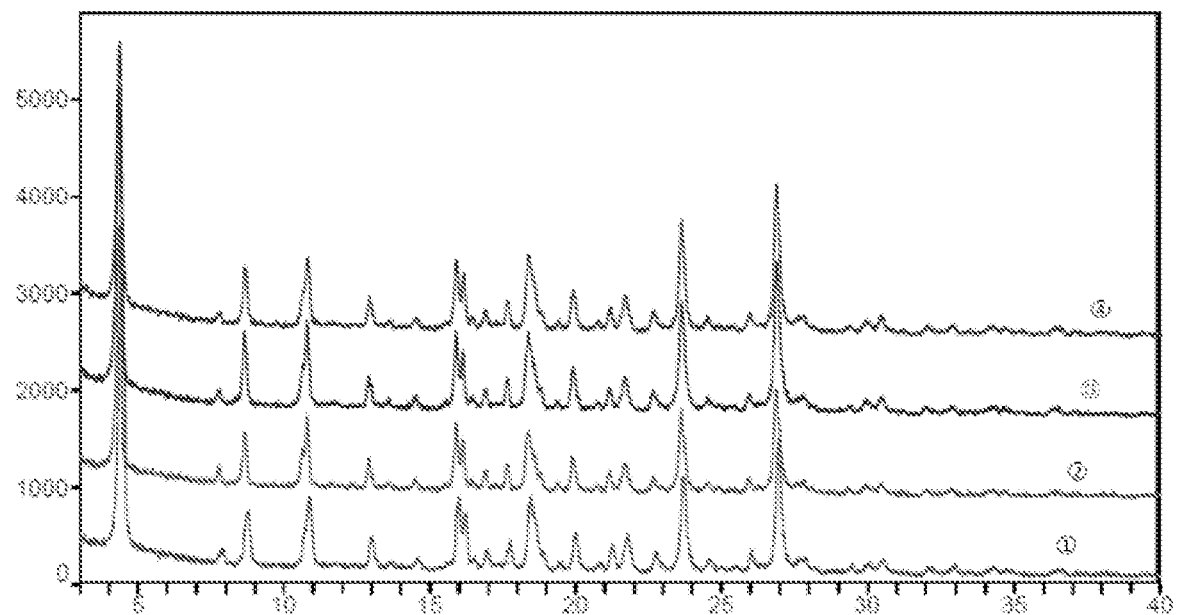
FIG. 10: XRD pattern of crystal form A of compound II (small sample, batch number: 1072P04-A14S01) at different stability conditions. From bottom to top, the means of lines ① to ④ respectively is depicted as follows:
① XRD pattern of crystal form A of compound II for 0 day;
② XRD pattern of crystal form A of compound II at 25° C., under humidity of 60% for 10 days;
③ XRD pattern of crystal form A of compound II at 40° C., under humidity of 75% for 10 days;
④ XRD pattern of crystal form A of compound II at 80° C., under drying condition for 24 h.
Figure 11:
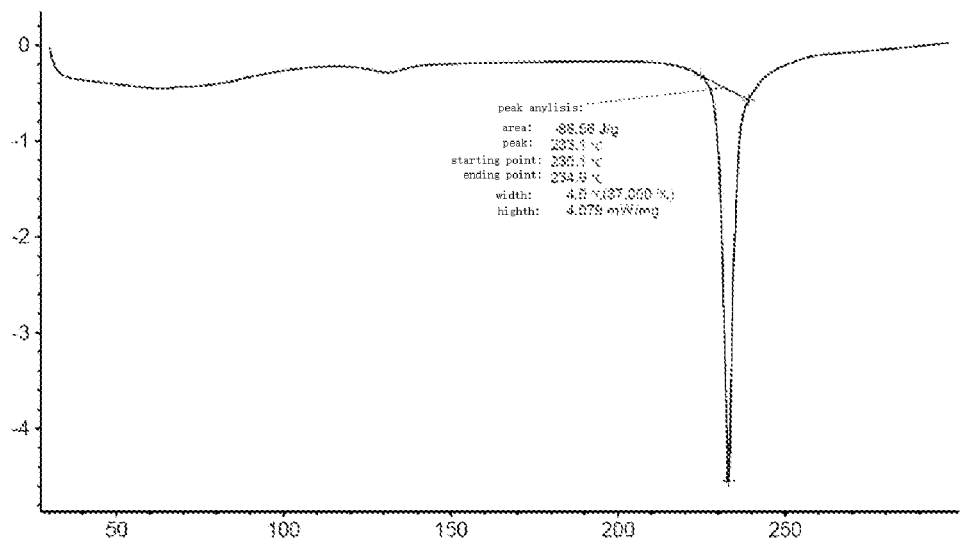
FIG. 11: DSC pattern of crystal form A of compound II. The abscissa (X-axis) represents temperature in units of ° C.; the ordinate (Y-axis) represents the heat flow in units of w/g.

The XRD pattern of crystal form A of compound II at different conditions was shown in FIG. 10. As shown in this figure, the crystal form A of compound II was dried at 80° C. for 24 h, 25° C., or 60% RH for 10 days, 40° C., 75% RH for 10 days, the crystal form was not changed, which showed that the crystal form A of compound II had a good stability.

In addition, the crystal form B of compound II was a metastable crystal form that was poorly crystal, and the crystal form B was heated to 180° C. which could be converted to crystal form A.

Example 4 Crystal Form Long-Term Stability Determination

Samples of crystal form A of compound I and compound II were placed at 25° C.±2° C., and a relative humidity of 60%±10% for 18 months, respectively. And samples were detected by HPLC at 0 month, 3 months and 18 months, respectively, and the results were as shown in table 6.

Table 6 the results of crystal form A compound I and compound II at 0 month, 3 months and 18 months detected by HPLC

| | | samples | |
|---|---|---|---|
| Detection Item | time | compound I | crystal formA of compound II |
| Maximum single impurity content (%) | 0 month | 0.04% | 0.05% |
| | 3 month | 0.10% | 0.05% |
| | 18 month | 0.22% | 0.06% |
| Total impurity content (%) | 0 month | 0.11% | 0.10% |
| | 3 month | 0.17% | 0.13% |
| | 18 month | 1.0% | 0.21% |
| Content > 0.1% Number of unknown impurities (s) | 0 month | 0 | 0 |
| | 3 month | 0 | 0 |
| | 18 month | 4 | 0 |

As shown in Table 6, it can be seen that after 18 months both the maximum single impurity content and the total impurity content of Compound I were more than 3 times that of the crystal form A of Compound II. The crystal form A of Compound II produces impurities in an amount less than 0.1% after 18 months, while compound I produced four impurities in an amount greater than 0.1%. The stability of the crystal form A of compound II was significantly improved compared to Compound I.

Example 5 Dynamic Moisture Sorption (DVS) Determination

The instruments and methods of Dynamic moisture adsorption in the present invention was shown in table 7, the results of DVS was shown in table 8.

TABLE 7 instruments and methods of Dynamic moisture adsorption

| device instruments | Dynamic moisture adsorption instrument(DVS) TA Instruments Q5000TGA | |
|---|---|---|
| Control software | Thermal Advantage | |
| Analysis software | Universal Analysis | |
| Sample tray | Platinum crucible | |
| Sample detection amount | 1-10 mg | |
| Protective gas | nitrogen | |
| flow rate of gas | 10 mL/min | |
| Criterion of judgment | Non-hygroscopic | No more than 0.2% |
| | Slight moisture absorption | more than 0.2%, but momore than 2.0% |
| | Easy moisture absorption | more than 2%, but nomore than 15% |
| | Extreme moisture absorption | more than 15% |

TABLE 8 the results of DVS

| crystal form of compound | Weight change in the range of 0% RH-80% RH |
|---|---|
| crystal form A of compound II | 5.3% |
| crystal form B of compound II | 5.5% |
| crystal form D of compound III | 17.2% |
| crystal form F of compound III | 16.6% |

The crystal form A and crystal form B of compound II: weight changes in the range of 0% RH to 80% RH were about 5.3% and 5.5%, while the crystal form D and crystal form F of compound III: weight changes in the range of 0% RH to 80% RH were about 17.2% and 16.6%. It can be seen therefrom that the crystal form of compound II is less hygroscopic than the crystal form of compound III and is more suitable for the preparation of solid formulations.

Example 6 Solubility Determination

Solubility tests were performed on the crystal form A of compound II, the crystal form D of compound III, and the compound I. The results of solubility in water at room temperature were shown in Table 9. It can be seen that different crystal forms of compound II have different properties of improvement in solubility, and the crystal form A of compound II exhibits excellent dissolution properties.

TABLE 9

Solubility results of different crystal forms of compound II

| crystal form of compound | solubility at room temperature in water | Classification of solubility |
| --- | --- | --- |
| crystal form A of compound II | 100-200 mg/mL | Readily-soluble |
| crystal form D of compound III | 50-100 mg/mL | soluble |
| compound I | <1 mg/mL | Very little soluble |

Note:
the classification standard of solubility follows the relevant provisions in the four general cases of «Pharmacopoeia of the people's replublic of China (2015)».

Example 7 Pharmacokinetic Experiment

A total of 12 SD rats were divided into two groups, 6 in each group, each half of male and female. 30 mg/kg of crystal form A of compound II and compound I were administrated orally by gavage once a day seperately.

In the above plasma sample, protein was precipitated by acetonitrile, the supernatant was diluted 3 times with water, and 5 μL was detected by LC-MS/MS, the results of experiment was shown in table 10:

TABLE 10 the results of pharmacokinetic experiment

| compound | Mode of administration | Doses (mg/kg) | $AUC_{last}$ (h*ng/mL) |
| --- | --- | --- | --- |
| compound I | PO | 30 | 27670 |
| crystal form A of compound II | PO | 30 | 47032 |

As shown in the table above, compared with to the compound I, the crystal form A of compound II was better absorbed in vivo.

Example 8 CDK4/6 Inhibition Assay of the Compound I

To demonstrate that the compounds exhibit affinity for CDK kinases (CDK4/CycD3, CDK6/cycD3), CDK kinases assays were performed.

Reaction buffers were prepared as follows: kinase base buffer for CDK6 (50 mM HEPES, pH7.5; 0.0015% Brij-35; 10 mM $MgCl_2$; 2 mM DTT); Kinase base buffer for CDK4 (20 mM HEPES, pH7.5; 0.01% Triton X-100; 10 mM $MgCl_2$; 2 mM DTT); Stop buffer (100 mM HEPES, pH7.5; 0.015% Brij-35; 0.2% Coating Reagent #3; 50 mM EDTA)

Enzyme Reaction Protocol:
1) Dilute the compound to 50× of the final desired highest concentration in reaction by 100% DMSO. Transfer 100 μL of this compound dilution to a well in a 96-well plate. Then, serially dilute the compound by transferring 30 μL to 60 μL of 100% DMSO in the next well and so forth for a total of 10 concentrations. Add 100 μL of 100% DMSO to two empty wells for no compound control and no enzyme control in the same 96-well plate. Mark the plate as source plate.
2) Prepare intermediate plate by transferring 10 μL of compound from source plate to a new 96-well plate containing 90 μL of kinase buffer as the intermediate plate.
3) Transfer 5 μL of compound from the 96-well intermediate plate to a 384-well plate in duplicates.
4) Add 10 μL of 2.5× enzyme solution to each well of the 384-well assay plate.
5) Incubate at room temperature for 10 min.
6) Add 10 μL of 2.5× substrate solution prepared by adding FAM-labeled peptide and ATP in the kinase base buffer. Reaction concentrations for enzymes and substrates as following table (table 11):

TABLE 11

Reaction concentration of enzyme and substrate

| Enzyme | Enzyme(nM) | ATP (μM) | Peptide | Peptide concentration(μM) |
| --- | --- | --- | --- | --- |
| CDK4 | 10 | 280 | P8 | 3 |
| CDK6 | 15 | 800 | P8 | 3 |

7) Incubate at 28° C. for specified period of time.
8) Add 25 μL of stop buffer to stop reaction.
9) Collect data on Caliper. Then convert conversion values to inhibition values.

Percent inhibition=(max−conversion)/(max−min)*100

"max" stands for DMSO control; "min" stands for low control herein.
10) Curve fitting using percent inhibition in XLFit excel add-in version 4.3.1 to obtain $IC_{50}$ values. Equation used is: Y=Bottom+(Top−Bottom)/(1+($IC_{50}$/X)^HillSlope).

The results are expressed as $IC_{50}$ value which is shown in table 12.

TABLE 12

CDK4/6 inhibitory activity assay results

| Sample | $IC_{50}$(CDK4)/nM | $IC_{50}$(CDK6)/nM |
| --- | --- | --- |
| LY2835219 | 2 | 22 |
| compound I | 1.9 | 22 |

Example 9 Inhibitory Activity and Selectivity Test on Other Subtypes of CDK Kinase at Molecular Level Compound I was used as a test compound, and compared with the positive control drug (Abemaciclib) to compare CDK kinase inhibitory activity and selective specificity between them.

The mechanism of this method is shown in formula (IV). The kinase catalyzes the phosphorylation of the protein substrate to label the $^{33}$P on the $^{33}$P-labeled ATP ($\gamma$-$^{33}$P-ATP) to the protein substrate in the reaction system, the reaction system was spotted on P81 ion-exchange membrane, and the membrane was washed extensively with 0.75% phosphate buffer; the radioactively-phosphorylated substrate was left on the membrane, and the kinase activity was reflected by recording the intensity of the substrate protein radiolabel.

Formula (IV)

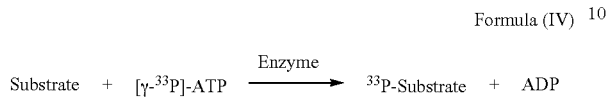

Data was processed with Prism4 Software (GraphPad), and the curve fitting formula was:

$Y$=Bottom+(Top−Bottom)/(1+10^((Log IC$_{50}$−$X$)*Hill-Slope)); wherein, $Y$ is percent inhibition (%); $X$ is logarithm of concentration of the inhibitor.

Results: Through the screening of various CDK kinases, it was found that the compound I have an IC$_{50}$ of greater than 0.4 μM for inhibiting CDK1/2/7/9, which is tens to thousands of fold higher than that of CDK4/6 (See table 13).

TABLE 13

CDK kinase inhibitory activity

| Kinases | IC$_{50}$(nM) | |
|---|---|---|
| | LY2835219 | compound 2b |
| CDK1/cyclin B | 308 | 1683 |
| CDK2/cyclin E | 90 | 441 |
| CDK7/cyclin H | 2071 | 664 |
| CDK9/cyclin T1 | 111 | 649 |

Conclusion: At the molecular level, the compound I of the present invention showed strong inhibitory effect on CDK4/6, and weak inhibitory effect on CDK1/2/7/9, indicating that the compound I is a CDK4/6 kinase inhibitor with excellent selectivity. In addition, the selectivity of compound I between CDK1/2/9 and CDK4/6 was significantly higher than that of LY2835219 (Abemaciclib).

Example 10 Tumor Regression Effect on JeKo-1 Xenograft Animal Model

JeKo-1 cells were cultured in RPMI 1640 medium containing 20% fetal bovine serum. Exponentially growing JeKo-1 cells were collected and resuspended in PBS to a suitable concentration for NOD/SCID mice subcutaneous tumor inoculation. 70 female mice were inoculated subcutaneously on the right with 5×10$^6$ JeKo-1 cells, resuspended in PBS and matrigel (1:1). When the average tumor volume reached 134 mm$^3$, the mice were randomly grouped according to the size of the tumor and were administrated. 48 mice were divided into the experimental group, and the remaining 22 mice were not used for experiment. Tumor volume is calculated as: long diameter×short diameter$^2$/2. The test was divided into solvent control group, test drug representative compound I (10 mg/kg), test drug representative compound I (25 mg/kg), test drug representative compound I (50 mg/kg), test drug representative compound I (100 mg/kg), a total of 6 groups with each of 8 mice, and the mice were administrated orally by gavage once a day and then continuous administration for 19 days. Efficacy is evaluated according to the relative tumor growth inhibition rate of TGI, the results was shown in table 14.

The calculation formula is as follows: TGI (%)=(C−T)/C×100% (C and T are the average tumor weight of the solvent control group and the average tumor weight of the treatment group, respectively). The higher the TGI (%) value illustrates the better the potency; and vice versa.

Results: compound I demonstrates excellent anti-tumor activity.

TABLE 14

Anti-tumor efficacy evaluation of representative compound I on JeKo-1 xenograft model

| Group | Dose (mg/kg) | Relative tumor growth inhibition rate TGI(%) | pValue$^a$ |
|---|---|---|---|
| Solvent control | — | — | — |
| compound I | 10 | 42.7 | 0.087 |
| compound I | 25 | 73.8 | 0.003 |
| compound I | 50 | 98.3 | 0.001 |
| compound I | 100 | 104.5 | 0.001 |

Note:
$^a$p value is the comparative analysis of tumor volume for the treatment group and the solvent control group.

The invention claimed is:
1. A crystal form of a compound as shown in Formula II:

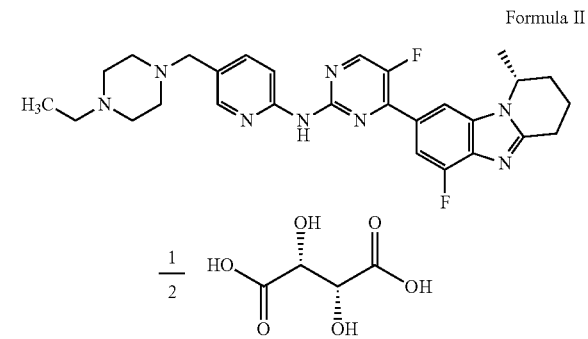

Formula II wherein, the X-ray powder diffraction pattern of the crystal form has characteristic peaks at the diffraction angle 2θ of 4.4±0.2°, 23.6±0.2° and 26.9±0.2°.

2. The crystal form according to claim 1, wherein, the X-ray powder diffraction pattern of the crystal form has characteristic peaks at the diffraction angle 2θ of 4.4±0.2°, 8.7±0.2°, 10.8±0.2°, 18.4±0.2°, 23.6±0.2° and 26.9±0.2°.

3. The crystal form according to claim 2, wherein, the X-ray powder diffraction pattern of the crystal form has characteristic peaks at the diffraction angle 2θ of 4.4±0.2°, 8.7±0.2°, 10.8±0.2°, 15.9±0.2°, 18.4±0.2°, 23.6±0.2° and 26.9±0.2°.

4. The crystal form according to claim 3, wherein, the crystal form approximately has an X-ray powder diffraction pattern as shown in FIG. 1.

5. The crystal form according to claim 3, wherein, the crystal form approximately has an X-ray powder diffraction pattern as shown in FIG. 12.

6. The crystal form according to claim 1, wherein, the crystal form is prepared by following steps:
  1) suspending (R)—N-(5-((4-ethylpiperazin-1-yl)methyl)pyridin-2-yl)-5-fluoro-4-(6-fluoro-1-methyl-1,2,3,4-tetrahydrobenzo[4,5]imidazo[1,2-a]pyridin-8-yl)pyrimidin-2-amine (Compound I) in water and/or a water-soluble organic solvent, obtaining a suspension;
2) heating the suspension to 50° C. or more;
3) keeping the temperature at 50° C. or more, adding L-tartaric acid to the suspension, and carrying out an acidification treatment, obtaining a clear solution; and
4) cooling the clear solution to room temperature, filtering while stirring, drying the filter cake, and obtaining the crystal form according to claim 1.

7. The crystal form according to claim 1, wherein, the crystal form is prepared by following steps:
dissolving Compound I in methanol at 50-70° C. to obtain a clear solution, dissolving L-tartaric acid in methanol, adding the solution of L-tartaric acid in methanol dropwise to the solution of Compound I in methanol, filtering after stirring, drying a filter cake at 40-70° C., and obtaining the crystal form according to claim 1.

8. A method for preparing the crystal form according to claim 1, comprising:

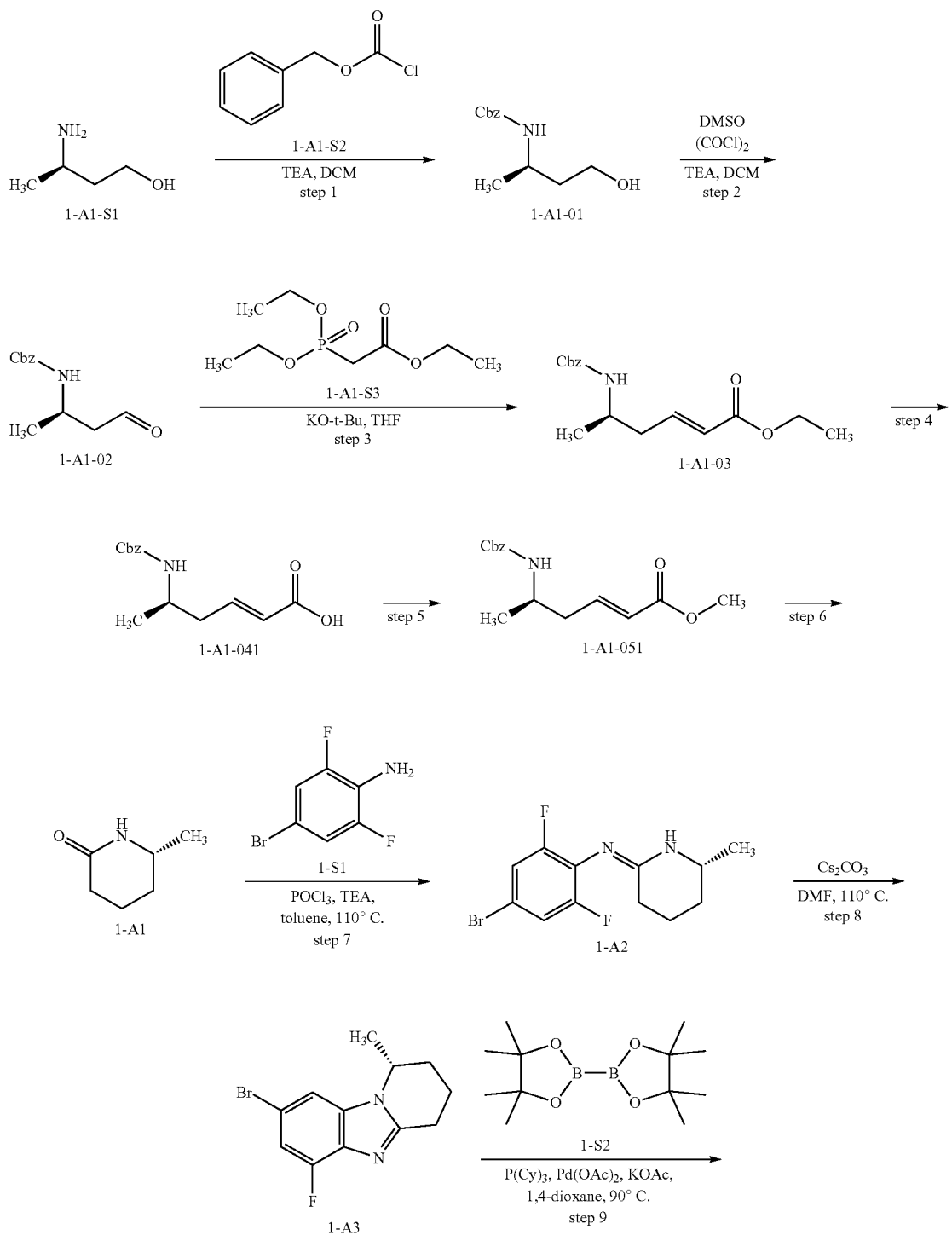

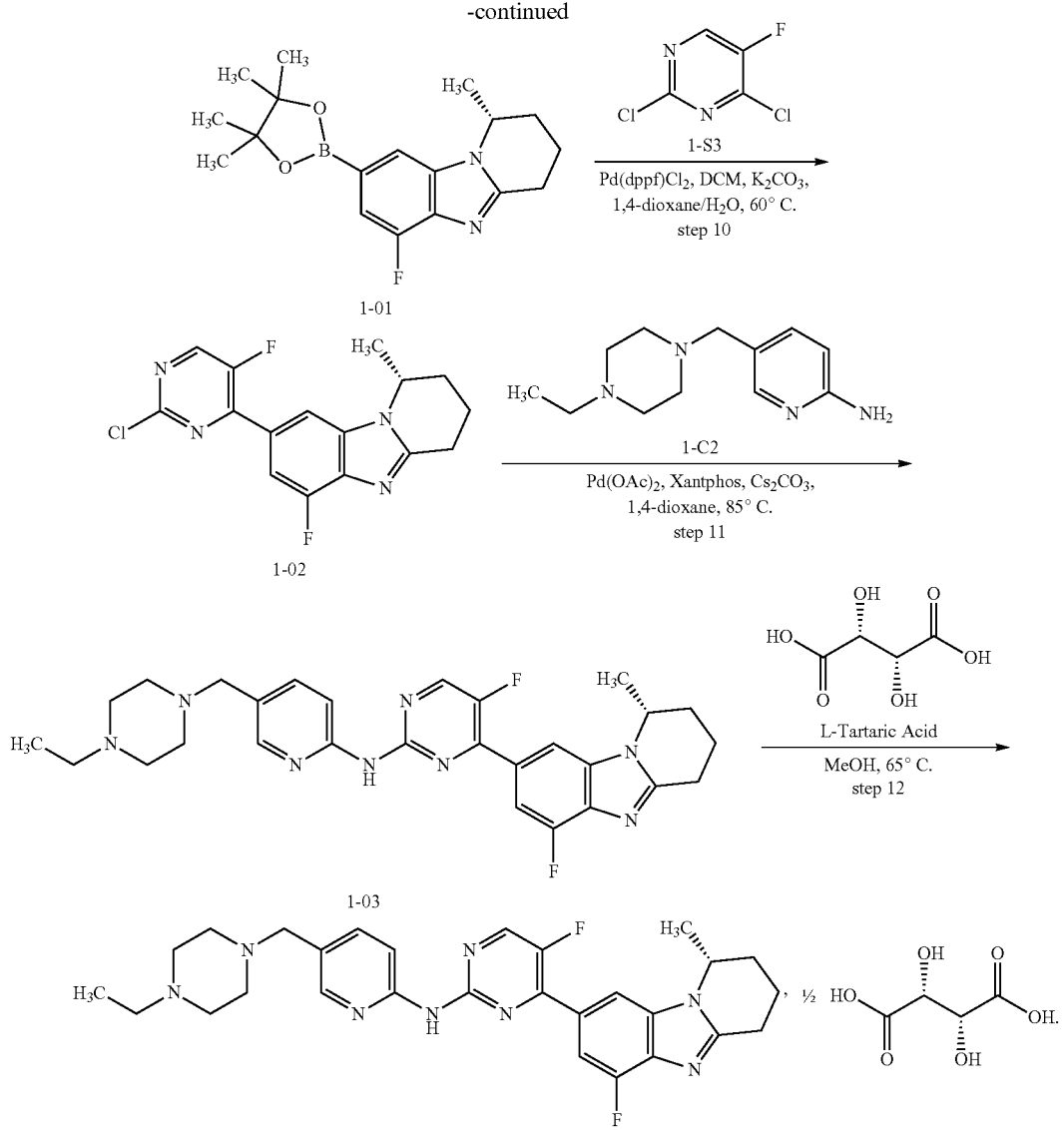
9. A pharmaceutical composition, comprising a therapeutically effective amount of the crystal form according to claim 1, and pharmaceutically acceptable excipients, auxiliaries and/or carriers.
* * * * *